US011631280B2

(12) United States Patent
Mouton et al.

(10) Patent No.: US 11,631,280 B2
(45) Date of Patent: Apr. 18, 2023

(54) SYSTEM AND METHOD FOR MULTIMODAL SPATIOTEMPORAL PAIN ASSESSMENT

(71) Applicant: University of South Florida, Tampa, FL (US)

(72) Inventors: Peter Randolph Mouton, Gulfport, FL (US); Sammie Lee Elkins, Tampa, FL (US); Md Sirajus Salekin, Tampa, FL (US); Dmitry Goldgof, Lutz, FL (US); Yu Sun, Tampa, FL (US); Thao Ho, Tampa, FL (US); Ghadh Alzamzmi, North Bethesda, MD (US)

(73) Assignee: University of South Florida, Tampa, FL (US)

(*) Notice: Subject to any disclaimer, the term of this patent is extended or adjusted under 35 U.S.C. 154(b) by 192 days.

(21) Appl. No.: 17/093,070

(22) Filed: Nov. 9, 2020

(65) Prior Publication Data
US 2021/0052215 A1 Feb. 25, 2021

Related U.S. Application Data

(63) Continuation-in-part of application No. 14/989,500, filed on Jan. 6, 2016, now Pat. No. 10,827,973.

(60) Provisional application No. 62/967,375, filed on Jan. 29, 2020, provisional application No. 62/186,956, filed on Jun. 30, 2015.

(51) Int. Cl.
*G06V 40/20* (2022.01)
*A61B 5/1171* (2016.01)
*G06V 40/16* (2022.01)

(52) U.S. Cl.
CPC ............ *G06V 40/23* (2022.01); *A61B 5/1176* (2013.01); *G06V 40/174* (2022.01)

(58) Field of Classification Search
CPC ...... A61B 5/4824; A61B 5/0013; A61B 5/746
See application file for complete search history.

(56) References Cited

U.S. PATENT DOCUMENTS 8,764,650 B2 7/2014 Schiavenato et al.
2006/0128263 A1 6/2006 Baird
(Continued)

FOREIGN PATENT DOCUMENTS

CN 107491740 A 12/2017
WO 2014036263 A1 3/2014

OTHER PUBLICATIONS

Lu, Guanming, Xiaonan Li, and Haibo Li. "Facial expression recognition for neonatal pain assessment." 2008 International Conference on Neural Networks and Signal Processing. IEEE, 2008. (Year: 2008).*

(Continued)

*Primary Examiner* — Amandeep Saini
*Assistant Examiner* — Raphael Schwartz
(74) *Attorney, Agent, or Firm* — Smith & Hopen, P.A.; Molly L. Sauter

(57) ABSTRACT

A computer-based system and method for generating a current pain assessment of a neonate using facial expressions along with crying sounds, body movement, and vital signs changes and for using the current pain objective assessment to predict future pain objective assessment and assign a future pain probability score by incorporation spatiotemporal data into the multimodal assessment.

20 Claims, 24 Drawing Sheets

(56) References Cited

U.S. PATENT DOCUMENTS

2008/0235030 A1* 9/2008 Sisto .................. G10L 17/26
 704/275
2014/0276188 A1 9/2014 Jardin

OTHER PUBLICATIONS

Arif-Rahu et al., Bio behavioral measures for pain in the pediatric patient. Pain Management Nursing 13.3 (2012): pp. 157-168.
Bagnato et al. Robust infants face tracking using active appearance models: a mixed-state condensation approach. Advances in Visual Computing. Springer Berlin Heidelberg, 2007. pp. 13-23.
Beauchemin et al., The computation of optical flow. ACM Computing Surveys (CSUR) vol. 27, No. 3 (1995): pp. 433-466.
Brahnam et al., Introduction to neonatal facial pain detection using common and advanced face classification techniques. Advanced Computational Intelligence Paradigms in Healthcare-1. Springer Berlin Heidelberg, 2007. pp. 225-253.
Brahnam, et al., Machine assessment of neonatal facial expressions of acute pain. Decision Support Systems vol. 43, No. 4 (2007): pp. 1242-1254.
Brahnam et al., Machine recognition and representation of neonatal facial displays of acute pain. Artificial intelligence in medicine vol. 36, No. 3 (2006): pp. 211-222.
Craig, K.D., et al., Pain in the preterm neonate: behavioural and physiological indices. Pain, 1993. vol. 52, No. (3): pp. 287-299.
Fournier-Charrière et al., Evendol, a new behavioral pain scale for children ages 0 to 7years in the emergency department: Design and validation. PAIN® vol. 153, No. 8 (2012): pp. 1573-1582.
Gholami et al., Agitation and pain assessment using digital imaging. Engineering in Medicine and Biology Society, 2009. EMBC 2009. Annual International Conference of the IEEE, 2009, pp. 1-13.
Hall et al., The WEKA data mining software: an update. ACM SIGKDD explorations newsletter vol. 11, No. 1, (2009) pp. 1-10.
Hammal et al., Automatic detection of pain intensity. Proceedings of the 14th ACM international conference on Multimodal interaction. ACM, 2012, pp. 1-6.
Hicks et al., The Faces Pain Scale-Revised: toward a common metric in pediatric pain measurement. Pain vol. 93, No. 2(2001): pp. 173-183.
Holsti et al., Specific Newborn Individualized Developmental Care and Assessment Program movements are associated with acute pain in preterm infants in the neonatal intensive care unit. Pediatrics, 2004. vol. 114, No. 1: pp. 65-72.
Hummel, P.A., et al., Clinical reliability and validity of the N-PASS: neonatal pain, agitation and sedation scale with prolonged pain. Journal of perinatology, 2003. vol. 28, No. 1, pp. 55-60.
Johnston et al., Experience in a neonatal intensive care unit affects pain response. Pediatrics vol. 98, No. 5 (1996): pp. 925-930.
Kohavi, A study of cross-validation and bootstrap for accuracy estimation and model selection. IJCAI, vol. 14. No. 2. 1995, pp. 1-8.
Lienhart et al., An Extended Set of Haar-like Features for Rapid Object Detection. IEEE ICIP 2002, vol. 1, pp. 900-903, Sep. 2002.
Lindh et al., Heel lancing in term new-born infants: an evaluation of pain by frequency domain analysis of heart rate variability. Pain vol. 80, No. 1 (1999): pp. 143-148.
Nanni et al., A local approach based on a Local Binary Patterns variant texture descriptor for classifying pain states. Expert Systems with Applications vol. 37, No. 12 (2010): pp. 7888-7894.
Saragih et al., Face alignment through subspace constrained meanshifts. In International Conference of Computer Vision, Sep. 2009, pp. 1-8.
Shreve et al., Automatic Expression Spotting in Videos, Image and Vision Computing, vol. 32, No. 8, pp. 476-486, 2014.
Shreve et al., Macro- and micro- expression spotting in long videos using spatio-temporal strain. International Conference on Automatic Face and Gesture Recognition, pp. 51-56, c 2012 IEEE, Mar. 2011.
Shreve et al., Towards macro- and micro-expressions spotting in videos using strain patterns. Workshop on Applications of Computer Vision, Dec. 2009, pp. 1-6.
Valeri et al., Pain in preterm infants: Effects of sex, gestational age, and neonatal illness severity. Psychology & Neuroscience. vol. 5, No. 1, pp. 11-19.
Viola et al., Rapid Object Detection using a Boosted Cascade of Simple Features. IEEE CVPR, 2001, pp. I-511-I-518.
Viola et al., Robust real-time face detection. International journal of computer vision vol. 57, No. 2, (2004): pp. 137-154.
Wilson et al., Facial feature detection using Haar classifiers. Journal of Computing Sciences in Colleges vol. 21, No. 4 (2006): pp. 127-133.
Evans et al., Longitudinal comparison of preterm pain responses to repeated heelsticks. Pediatric nursing, 2005. vol. 31, No. 3: pp. 216-221.
Fotiadou et al., Video-based facial discomfort analysis for infants, Proc. SPIE 9029, Visual Information Processing and Communication V, 90290F, 2014, pp. 1-14.
Gibbins, S., et al., Comparison of pain responses in infants of different gestational ages. Neonatology, 2008. vol. 93, No. 1: pp. 10-18.
Hudson-Barr et al., Validation of the pain assessment in neonates (PAIN) scale with the neonatal infant pain scale (NIPS). Neonatal Network. vol. 21, No. 6: pp. 15-21.
Petroni, Marco, et al. Identification of pain from infant cry vocalizations using artificial neural networks (ANNs). SPIE's 1995 Symposium on OE/Aerospace Sensing and Dual Use Photonics. International Society for Optics and Photonics, vol. 2492, pp. 729-737.
Brahnam et al., Neonatal Facial Pain Detection Using NNSOA and LSVM. Ipcv. 2008, pp. 1-7.
Anand, Consensus statement for the prevention and management of pain in the newborn. Archives of pediatrics & adolescent medicine vol. 155, No. 2, (2001): pp. 173-180.
Allegaert et al., Variability in pain expression characteristics in former preterm infants, J. Perinat. Med. vol. 33, No. 5, (2005) pp. 442-448.
Hummel et al., N-PASS: Neonatal Pain, Agitation and Sedation Scale—Reliability and Validity, Poster presented at: the Pediatric Academic Societies annual meeting, Pediatrics/Neonatology, Loyola University Medical Center, Maywood, IL Perinatal Center, Oncology Institute, vol. 2, N. 6, Nov. 2004, pp. 1-4.
Lawrence, The development of a tool to assess neonatal pain. Neonatal network: NN vol. 12, No. 6, (1993): pp. 59-66.

* cited by examiner

Mathematical Formulation of the Isolated Acute Pain Model

Let:
$X_1$ = facial expression, (0-1)
$X_2$ = vital signs, (0-1)
$X_3$ = crying, (0-1-2)
$X_4$ = body motions, (0-1)
$X_5$ = state of arousal, (0-1)

Then, the multivariable regression model can be defined as:
$Y_p = b_1X_1 + b_2X_2 + b_3X_3 + b_4X_4 + b_5X_5 + b_0$ Where: $Y_p$ = response variable (i.e., total pain score (0-7))
$X_{1-5}$ = predictor variables (i.e., features vectors)
$b_{1-5}$ = the features' coefficients or weights, and
$b_0$ = error.

*The values of these weights can vary based on the infant's group*

Pain Threshold = 
(PT)
$\begin{cases} \text{If } Y_p = 0\text{-}2, \text{ No pain} \\ \text{If } Y_p = 3\text{-}4, \text{ Moderate pain} \\ \text{If } Y_p >= 4, \text{ Severe pain} \end{cases}$

*FIG. 12A*

Mathematical Formulation of the Prolonged Acute Pain Model

Let:
$X_1$ = facial expression, (0-2)
$X_2$ = vital signs, (0-2)
$X_3$ = crying, (0-2)
$X_4$ = body motion, (0-2)
$X_5$ = state of arousal, (0-2)

Then, the multivariable regression model is defined as:
$Y_p = b_1X_1 + b_2X_2 + b_3X_3 + b_4X_4 + b_5X_5 + b_0$ Where: $Y_p$ = response variable (i.e., total pain score (0-10))
$X_{1-5}$ = predictor variables (i.e., features vectors)
$b_{1-5}$ = the features' coefficients or weights, and $b_0$=error.

*The values of these weights can vary based on the infant's group*

Group 1:
PT = $\begin{cases} \text{If } Y_p >= 6, \text{ Pain} \\ \text{Otherwise, No pain} \end{cases}$ Group 2:
PT = $\begin{cases} \text{If } Y_p >= 5, \text{ Pain} \\ \text{Otherwise, No pain} \end{cases}$ Group 3:
PT = $\begin{cases} \text{If } Y_p >= 4, \text{ Pain} \\ \text{Otherwise, No pain} \end{cases}$ Group 4:
PT = $\begin{cases} \text{If } Y_p >= 3, \text{ Pain} \\ \text{Otherwise, No pain} \end{cases}$

*FIG. 12B*

SYSTEM AND METHOD FOR MULTIMODAL SPATIOTEMPORAL PAIN ASSESSMENT

CROSS-REFERENCE TO RELATED APPLICATIONS

This application is a continuation-in-part of U.S. patent application Ser. No. 14/989,500 filed on Jan. 6, 2016, which claims priority to U.S. Provisional Patent Application No. 62/186,956 filed on Jun. 30, 2015. This application also claims priority to U.S. Provisional Patent Application No. 62/967,375 filed on Jan. 29, 2020, all of which are incorporated by reference in their entirety.

BACKGROUND OF THE INVENTION

For newborns of all birth weights in the United States, there is a trend toward increased likelihood of admission to the Neonatal Intensive Care Unit (NICU). The availability of highly specialized care for treatment of various healthcare emergencies raises the probability that premature and sick infants will survive. However, hospitalization of newborns for life-threatening illnesses requires repeated episodes of acute and/or prolonged pain from surgery and other types of tissue trauma. A major challenge for the scientific community is to mitigate the adverse effects of post-surgical pain on newborns, given their inability to verbally express pain, the vulnerability of their developing nervous system and the effects of pain and pain management on the structural and functional changes that take place during the early neonatal period.

Postoperative pain affects a large number of patients across the world, with an estimated number of 234 million surgical procedures each year. In the case of neonates, more than 1.5 million anesthetics are performed every year in the United States for surgical procedures such as gastrostomy tube placement and circumcision. This leads to the publications of a large body of research articles and guidelines in recent years to discuss optimal approaches for assessing and managing postoperative pain. Despite this significant attention, the management of postoperative pain has remained inadequate. This poor management is the main cause of delayed hospital discharge, which leads to substantial emotional and financial burden. In addition, it has been found that the poor management of postoperative pain can lead to serious short-term complications and long-term physiological, behavioral, and cognitive sequelae. As accurate pain assessment is the cornerstone for adequate management, it is critical to develop accurate pain assessment tools to obtain optimal interventions.

Broadly, pain in neonates can be categorized into three types: acute procedural, acute prolonged, and chronic. Usually, prolonged acute pain (aka., postoperative pain) occurs after a major surgery (i.e. omphalocele repair), lasts for a longer time compared to acute procedural, and repeats with a decreasing rate after the surgery. The current practice for assessing neonatal pain after a major surgery is manual and requires caregivers to observe specific behavioral (e.g., facial expression and body movement) and physiological (e.g., heart rate) indicators. Each of these indicators is assigned a score and the total pain score is generated by summing all the scores together. There are at least 29 validated score-based tools for manually assessing procedural and postoperative pain in neonates, and more than half of these scales are multidimensional. The multidimensional pain assessment is necessary because pain manifests itself in various behavioral and physiological signals. Several studies have reported that pain has at least two dimensions and suggested the use of multidimensional scales for effective assessment.

In addition, the multidimensional approach for assessment allows for the detection of pain during the failure of recording a specific pain indicator due to developmental (e.g., facial nerve palsy), clinical (e.g., sedation), and environmental (e.g., background noise) factors, and also captures individual differences in pain reactions. The score-based multidimensional scales of procedural pain have a narrower range of scores (pain vs. no-pain) as this type of pain tends to be intense for a short period of time and disappears as soon as its cause (e.g., heel lancing) is gone. On the contrary, acute prolonged (postoperative pain), or pain after any major surgery, continues long after its cause is gone, tends to have fluctuations in pain intensity, and evolves in a more complex pattern over time.

The current practice for pain assessment using multidimensional score-based scales is discontinuous, inconsistent and suffers from high inter-observer and intra-observer variations. To mitigate these limitations, several artificial intelligence-based methods have been published in the literature. However, few of the known method focus on assessing postoperative pain.

Machine learning-based systems are known in the art for continuous and objective detection of procedural pain in either pediatric intensive care units (PICU) or neonatal intensive care units (NICU). Previous work by the inventors shows that this approach can achieve a high degree of accuracy as evidenced by strong correlation with clinical ratings of acute pain by experts. However, in the approximately 500,000 neonate admissions per year in the United States, only about 1 in 3 receive correct pain management. By 2010, the most common drugs used to treat post-surgical pain and anxiety in the NICU were the highly addictive narcotics (opioids) that require prolonged withdrawal prior to discharge and a range of non-addicting benzodiazepines, barbiturates, ketamine, propofol, acetaminophen, and local and topical anesthetics. Today, the opioids morphine and fentanyl, a fast-acting narcotic that is 20-40× and 100× more potent than heroin and morphine, respectively, remain the cornerstone drugs for the therapeutic management of post-surgical pain in NICUs worldwide. These trends emphasize the importance to explore novel opioid-sparing strategies for the therapeutic management of neonatal pain in NICU.

Accordingly, there is a need in the art for a system and method that effectively and efficiently expands upon pain assessment techniques known in the art to additionally provide multimodal, spatiotemporal, pain assessment and in particular early pain detection (EPD) in neonates, thereby reducing unmanaged and undermanaged procedural pain in neonates.

SUMMARY OF INVENTION

In various embodiments, the present invention provides for a multimodal and spatiotemporal system and method for pain assessment of neonates.

In a particular embodiment, Early Pain Detection (EPD) in neonates is provided and additionally a confidence score (probability), similar to that provided by modern methods for predicting the weather is determined. For example, rather than gathering variables for weather prediction, e.g. "there's a 90% chance of rain in ~25 minutes," the machine learning-based methods of the present invention utilize the neonate's facial expressions, body movements, crying frequency and vital sign data (heart rate, blood pressure, oxygen saturation level) to assign a probability of experiencing pain, e.g. "there's a 90% chance this neonate will experience prolonged surgical pain in ~25 minutes."

In a particular embodiment, a system for providing EPD in neonates includes various hardware components, which may consist of two or more Go-Pro cameras with audio, camera stands, a computer with GPU board and associated cables.

The system and methods of the present invention reduce unmanaged and undermanaged procedure pain in neonates. By reducing unmanaged and undermanaged procedural pain in neonates, Early Pain Detection (EPD) is expected to mitigate the short-term and long-term impact of toxic stress on neonates.

Specifically, EPD is a medical device providing for continuous and objective monitoring of neonatal pain that will allow ~30 minutes prior to pain onset for pain mitigation using non-addicting drugs, including, but not limited to, Tylenol and nonsteroidal anti-inflammatory drugs (NSAIDS), rather than relying on opioid medications, such as fentanyl and morphine. If EPD can reduce or avoid the need for severe pain and opioid medications in the majority of cases, the EPD device of the present invention could substantially reduce the consequences of long-lasting toxic stress trauma including behavioral impairments, epigenetic modifications and increased complications caused by extreme pain and opioid addiction. Finally, it is expected that EPD will achieve these treatment goals while decreasing the economic burden on patients, private hospitals and government agencies by reducing the length of stay for treatment of opioid withdrawal.

In a specific embodiment, the current invention is a system for measuring or evaluating pain intensity experienced by a subject that is incapable clearly orally communicating the pain or that is capable of communicating the pain through only a behavioral indicator (e.g., an infant, an individual with dementia, etc.). The system includes a data reading device (e.g., A/V recorder such as a camera and/or microphone, vital signs reader) for visualizing and recording the subject's facial expressions, infant's voice, vital signs readings, and body movement including arms/legs. A facial expression classifier is used for evaluating the pain via the subject's facial expressions, where the facial expression classifier produces a facial expression score based on the subject's facial expressions. A voice classifier is used for evaluating the pain via the inarticulate sounds made by the subject (e.g., an infant's crying), where the voice classifier produces a voice score based on the frequency and pitch of those inarticulate sounds (e.g., using speech signal analysis). A vital signs classifier is used for evaluating the pain via the subject's physical condition (e.g., heart rate, breathing rate, oxygen saturation, changes in cerebral deoxyhemoglobin concentration, etc.), where the vital signs classifier produces a vital signs score based on the subject's physical condition. The system further includes a processor that runs a machine learning algorithm (e.g., parametric, non-parametric, optical flow, facial strain, local binary patterns, linear predictive coding, linear regression, neural network) for processing images, videos, signals, and/or a combination thereof. The facial expression score, voice classifier score, body motions score, and vital signs score are combined/weighed to produce a total score for pain assessment. The system also includes an output device for outputting the total score for pain assessment. Optionally, if the total score exceeds a predetermined threshold, a therapy or intervention can automatically be indicated by the output device as well.

Optionally, a body movement classifier may be used for evaluating the pain via the subject's motions that may correspond to the pain, where the body movement classifier produces a body movement score based on these motions. In this case, the body movement score would be combined with the other scores as well for the total score. These motions could indicate the subject's behavior state, arousal state, and extremities tone.

The facial expression classifier may evaluate pain intensity based on the subject's facial strain. Further, the facial strain can be trained using k Nearest-Neighbor and support vector machine for pain or no-pain experienced by the subject. Alternatively or in addition, detection of the facial strain can be accomplished via a modified strain algorithm predicated on movement of the subject's face.

The facial expression classifier may segment the subject's face into regions in order to provide the facial expression score even when a segment of the subject's face is obstructed or occluded. This permits partial facial detection.

Alternatively, or in addition, the facial expression classifier may include (1) facial detection where the subject's face is detected, (2) expression segmentation where the subject's face is segmented into regions, and (3) expression recognition where pain can be detected. The facial detection may be achieved by detecting landmarks on the subject's face. For example, a landmark can be the subject's nose, in which case a digital mask is expanded around the nose to also include the eyes and surrounding area of the face. The facial detection function may train the facial expression classifier with positive images including these landmarks and negative images that do not include the landmarks. Alternatively, or in addition, the facial detection function may train the facial expression classifier using an adaptive boosting algorithm.

During expression segmentation, there may be four (4) regions, wherein an optical flow vector generated for each region for the subject's face, such that the optical flow vector is used to estimate optical strains, which are then summed to generate an overall strain magnitude. This overall strain magnitude is related to the facial expressions that can indicate pain experienced by the subject.

Expression recognition may be achieved by applying a peak detector to detect points of maximum strain, wherein the maximum strain is related to the facial expressions that can indicate the subject's pain.

Regarding the voice classifier, frequency-based features may be extracted from the inarticulate sounds to represent audio segments that are used to train the voice classifier.

In a separate embodiment, the current invention may include any one or more—or even all—of the foregoing features and characteristics of the system.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 1A depicts strong head movement; FIG. 1B depicts self-occlusion; and FIGS. 1C-1D depict occlusion by external items such as a toy and a pacifier. Eyes are masked to protect privacy.

FIGS. 12A-12B depict the models' mathematical formulations, according to certain embodiments of the current invention.

DETAILED DESCRIPTION OF THE INVENTION

Figure 1A:
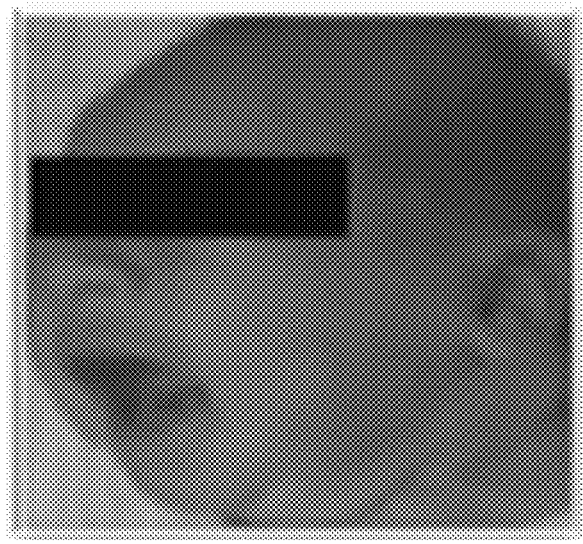
FIGS. 1A-1D are a series of images depicting examples of challenges of tracking and detecting facial expression in a real-time clinical setting.
Figure 1B:
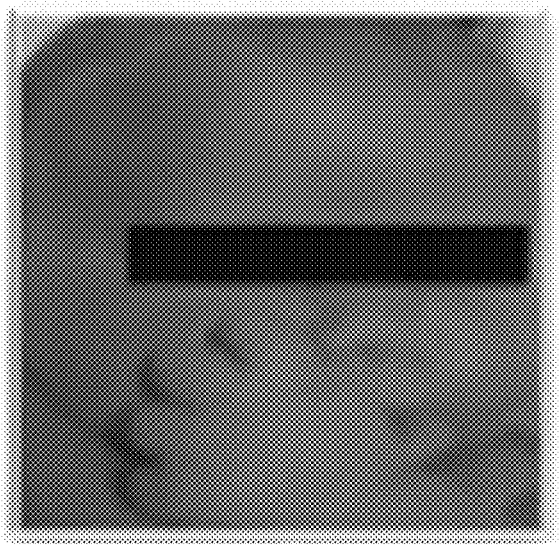
Figure 1C:
Figure 1D:

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

The current practice for assessing neonatal postoperative pain relies on bedside caregivers, is subjective, inconsistent, slow, and discontinuous. To develop a reliable medical interpretation, several automated approaches have been proposed to enhance the current practice. These approaches are unimodal and focus mainly on assessing neonatal procedural (acute) pain. As pain is a multimodal emotion that is often expressed through multiple modalities, the multimodal assessment of pain is necessary, especially in the case of postoperative (acute prolonged) pain. In addition, spatiotemporal analysis is more stable over time and has been proven to be highly effective at minimizing misclassification errors.

In various embodiments, the present invention provides a novel multimodal spatiotemporal approach that integrates visual and vocal signals and uses them for assessing neonatal postoperative pain.

As illustrated herein by experimental results, on a real-world dataset, the proposed multimodal spatiotemporal approach achieves the highest AUC (0.87) and accuracy (79%), which are on average 6.67% and 6.33% higher the than unimodal approaches. The results also show that the integration of temporal information markedly improves the performance as compared to the non-temporal approach as it captures changes in the pain dynamic. These results demonstrate that the proposed approach can be used as a viable alternative to the manual assessment, which would tread a path toward fully automated pain monitoring in clinical settings, point-of-care testing, and homes.

In an embodiment, the current invention is a method and system for assessing pain in an infant or other subject/individual who is incapable of clearly orally communicating pain levels/intensity. Specifically, a method and associated algorithm were developed for using an infant's facial expressions to determine a pain score using a modified strain algorithm. Unexpected results were obtained utilizing infant facial tissue distortion as a pain indicator in video-sequences of ten (10) infants based on analysis of facial strain. Facial strain, which is used as the main feature for classification, is generated for each facial expression and then used to train two classifiers, k Nearest-Neighbors (KNN) and support vector machine (SVM), to classify infants' expressions into two categories, pain and no-pain. The accuracy of binary classification for KNN and SVM was 96% and 94%, respectively, based on the ten (10) video sequences.

One challenge for the next generation of NICU-based pain management approaches is proactive pain mitigation (avoidance) aimed at preventing harm to neonates from both post-surgical pain and opioid withdrawal. Like AI-based methods for making reliable predictions of weather and climate events, AI-based frameworks can use single or multiple combinations of continuous objective variables, e.g., facial and body movements, crying frequencies and physiological data (vital signs), to make high-confidence predictions about time-to-pain onset. Such predictions would create a therapeutic window prior to pain onset for mitigation with non-narcotic (non-addicting) pharmaceutical and non-pharmaceutical interventions. These emerging AI-based strategies have the potential to minimize or avoid damage to the neonate's body and psyche from post-surgical pain and opioid withdrawal.

In contrast to pain assessment at a single point of time, an AI tool for predicting time to pain onset creates an opportunity to intervene with both non-opioid and non-pharmaceutical approaches prior to pain onset. This system and method of the present invention can monitor single or multiple combinations of continuous objective variables, e.g., facial and body movements, crying frequencies and physiological data (vital signs, and brain activity), to make high-confidence predictions about time-to-pain onset in neonates. Such predictions create a therapeutic window prior to pain onset for mitigation with non-narcotic (non-addicting) pharmaceutical and non-pharmaceutical interventions. The early prediction of pain has the potential to minimize or avoid damage to the neonate's body and psyche from postsurgical pain while decreasing the economic burden on patients, private hospitals and government agencies by reducing the length of stay for treatment of opioid withdrawal. The early pain prediction method of the present invention can be extended to continuously monitor and predict future pain of non-verbal children, adults with speech impairment and intubated patients.'

In an embodiment, the current invention is a machine-based infant pain assessment tool and methodology developed based on a series of behavioral and physiological pain indicators. This tool monitors infants continuously, detects various pain indicators (e.g., facial expression of pain, crying, body motion and changes in heart rate), and generates a total pain score based on these indicators.

In practice, this tool may be used in neonatal intensive care unit (NICU) to reduce clinical assessment subjectivity and reduce the costs of continuous monitoring of infants. It also can be used as a home-monitoring tool or in developing countries, where there is a lack of medical workers/supplies.

The novel system monitors infants at all times (not just during a certain procedure or period) using an audio/video recorder, as opposed to the input sensors seen in the prior art. Specifically, the audio/video recorder is used to visualize and record facial expressions, voice, state of arousal, and body movement including arms/legs. The use of the audio/video recorder as opposed to input sensors (e.g., flexure input sensors) is important because pain expression should be recognized by considering other parts of the face, not just the mouth. It is an object of the present invention to assess infants' pain on video sequences by utilizing multiple inputs, for example infants' facial expression of pain. It presents unexpected results for infants' pain assessment based on analysis of facial strain. The present invention is the first to address assessing infants' pain dynamically for monitoring purposes based on this type of analysis.

Certain embodiments of the current invention also utilize image/video/signal processing and machine learning techniques to generate an executable code to measure an infant's pain intensity continuously. This technique, when used, is known in the art to be very different from using Boolean logic or neural network to process the input data. The data from the instant invention is capable of generating a total score that can be sent wirelessly to a remote station or be displayed digitally or visually on the infant's incubator. The system can be used both in clinical settings and in non-clinical settings, as skin electrodes and other medical devices are not typically utilized.

In certain embodiments, the system includes an algorithm generally based on the strain algorithm, which is predicated on motion, requires no pre-training and segments the face into regions, allowing for partial facial recognition. Partial facial recognition is important because infants are frequently moving and often have one or more parts of their faces obstructed. In addition, the pain assessment system of the instant invention uses multiple inputs for infant pain such as vital signs, body movement, and voice (e.g., cry), as well as facial expression, to generate a total pain score.

It should be noted that the instant invention is directed towards individuals who cannot communicate their pain in any way other than a behavioral indicator, such as facial expression, body motion, crying, etc. Examples of such an individual include, but are not limited to, infants, individuals who are mute, individuals with communicative/neurologic impairments (e.g., dementia), etc.

Novel, unexpected results of utilizing facial expression as a behavioral indicator of pain were found herein. The method has three main stages—face detection, expression segmentation, and expression recognition. Manual detection of an infant's face was performed at the beginning to extract facial points and were used for cropping and registration. A strain algorithm was employed to segment expressions by exploiting the non-rigid facial motion that occurs during facial expressions. The accuracy of classifying the segmented expressions as pain or no-pain using KNN and SVM was 96% and 94%, respectively. Pain was assessed dynamically using infants' facial expression based on facial strain analysis.

A challenging set of infants' video sequences was collected for the purpose of building a real-time pain assessment system. The procedure for collecting the data complied with the protocols and ethical directives for research involving human subjects at the University of South Florida. Prior to data collection, informed consent was obtained from the infants' parents.

Video sequences for a total of 10 subjects older than 30 weeks gestational age (e.g., premature and infants) were recorded under two different pain conditions: acute and chronic. The video sequences of nine (9) subjects were recorded during the acute pain procedure, and the remaining one (1) was recorded during the chronic pain procedure.

As noted, the video sequences were recorded during two pain procedures: the acute and chronic pain procedures. Acute pain recordings were carried out during heel lancing procedures that were previously scheduled for routine blood test. Nine (9) subjects were recorded during the acute pain procedure in the presence of nurses who filled the score sheets using NIPS (Neonatal Infant Pain Scale) scoring tool. The scores were taken prior to, during, and after the procedure. These scores were used as ground-truth, which were compared later to the results of the method.

The infant with chronic pain was monitored during the post-operative recovery for approximately two (2) hours in the presence of nurses who scored the pain using an NPASS (Neonatal Pain, Agitation, and Sedation Scale) scoring tool at different intervals.

Table I summarizes the recording procedure for acute and chronic pain.

TABLE I

Summary of acute and chronic pain procedures.

| | Acute Pain | Chronic Pain |
|---|---|---|
| Pain Trigger | Immunization and heel lancing | Postoperative: G tube[1] |
| Pain Scale | NIPS | NPASS |
| Procedure | Acquire the infant's behavioral/physiological data before the pain procedure, at the start of the pain procedure, and after the completion of the procedure. NIPS pain scores were taken prior to, during, and after the acute procedure | Acquire the infant's behavioral/physiological data at the normal state before the operation and during post-operative periods for 15pprox . . . 2 hours. NPASS pain scores were taken during the post-operative period every 15 minutes. |

[1] a tube is inserted into the infant stomach for the purpose of feeding her/him.

In an embodiment, the instant pain expression recognition method includes three stages:
  A. Detection of an infant's face in video sequence followed by preprocessing operations including face alignment.
  B. Expression segmentation.
  C. Expression recognition or classification.

The first stage in developing a pain recognition system is detecting and tracking an infant's face in a video sequence. There are several known face detection algorithms that can detect and track faces with high accuracy. Most of these algorithms perform well in detecting adult faces, but fail in cases of infants due to several reasons, including the fact that existing algorithms are developed and trained based on adult faces, which have different features than infants' faces. Further, detecting infants' faces is a challenging problem because infants make unpredictable movements (i.e., infants make different and strong out-of-plane head movements) and occlude their face (i.e., self-occlusion by hand or occlusion by external items such as a pacifier). As such, these conventional face detection mechanisms have significant difficulties detecting and tracking infants' faces.

FIGS. 1A-1D show examples of these challenges. In the current study, the results of applying several face tracking implementations on the infants' video sequences were not satisfactory. For instance, the results of running the mean shift face tracker, which is a robust face tracker to automatically detect and track 66 points on the face were insufficient. The results of running a MATLAB's implementation of Viola-Jones were also insufficient.

Figure 2A:
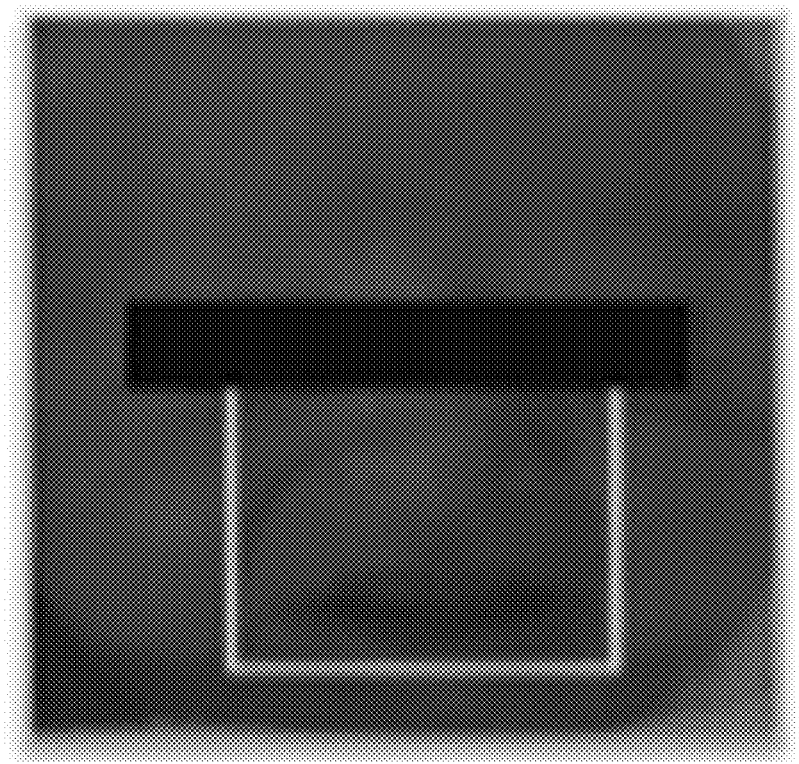
FIGS. 2A-B are a series of images depicting that the nose is detected first and then the mask is expanded to include the eyes and surrounding areas. This image depicts the manual face tracking that was used at the beginning of the study. An automated algorithm is now used to detect the face.
Figure 2B:
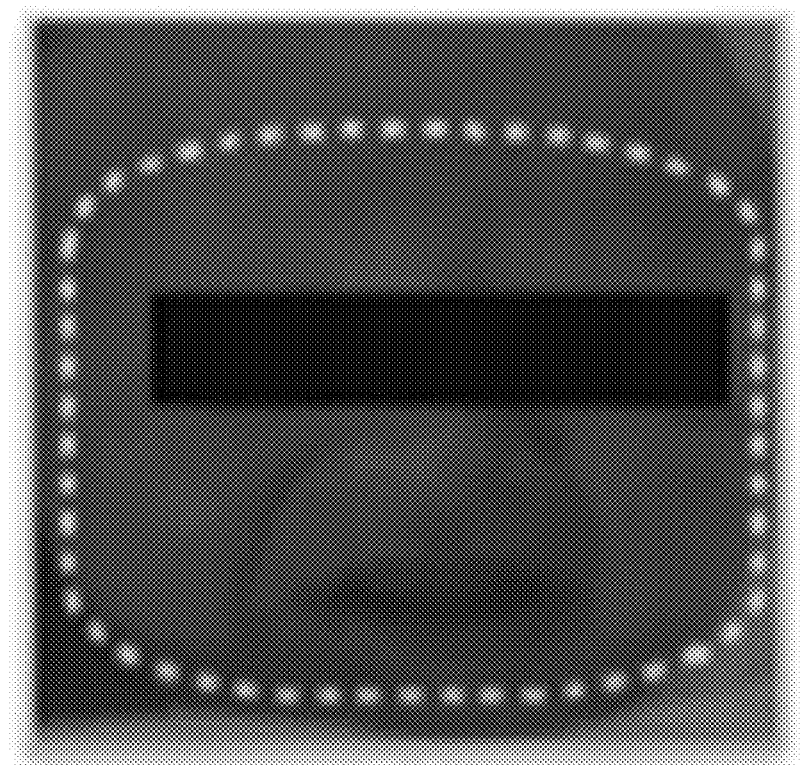

Due to these results and the difficulties of using conventional face detection software with infants, the landmark points of the infants' face were manually extracted by first detecting their nose (see FIG. 2A) using the MATLAB's implementation of a cascade object detector. Even though the nose detector was trained for adults, the detector was able to accurately detect infants' nose. The mask around the nose was then expanded to include eyes and the surrounding area, as seen in FIG. 2B. After faces are located, face alignment was performed by transferring each face image in a video sequence to match the original starting location of the face.

Figure 5:
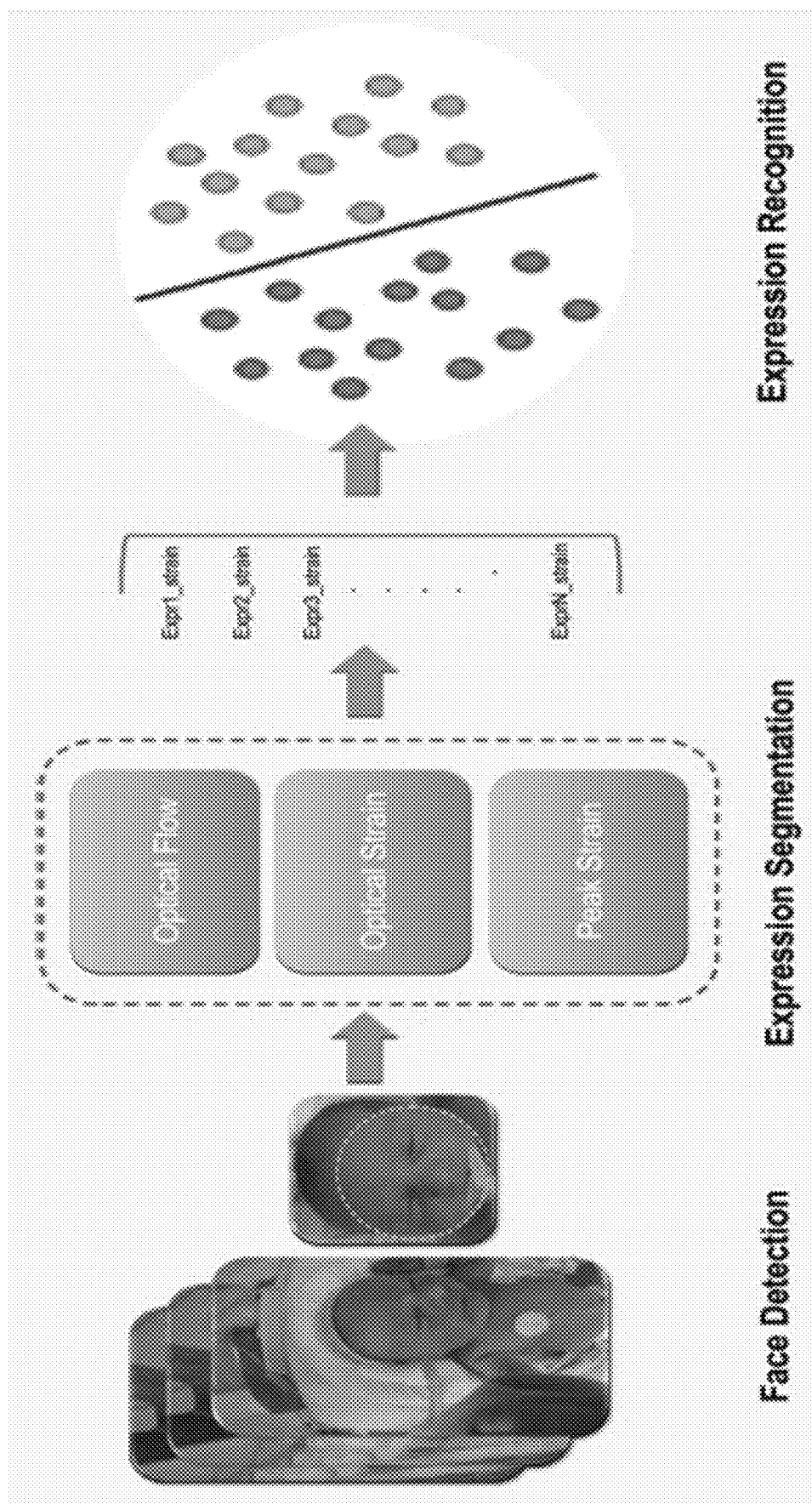
FIG. 5 is an image depicting the three stages of the machine-based infant pain expression recognition system: face detection, expression segmentation and expression recognition/classification.

Algorithms are known in the art to segment any expression in a video sequence by capturing the optical strain corresponding to elastic distortions of facial skin tissue. The facial optical strain can be derived directly from the vectors of optical flow, which is a well-known motion estimation technique based on the brightness conservation principle. The facial strain algorithm can be summarized as follows (also see FIGS. 5 & 8):
  A. Take a video sequence as input and locate sixty-six facial points in each frame. These points are used to align the face, crop it, and divide it into four regions.
  B. Generate an optical flow vector for each region of the face over all frames and use this vector to estimate the optical strain.
  C. Add the estimated strain values for each region together to generate the overall strain magnitude.
  D. Apply a peak detector to detect the points of maximum strain magnitude, which correspond to facial expressions.

Figure 8:
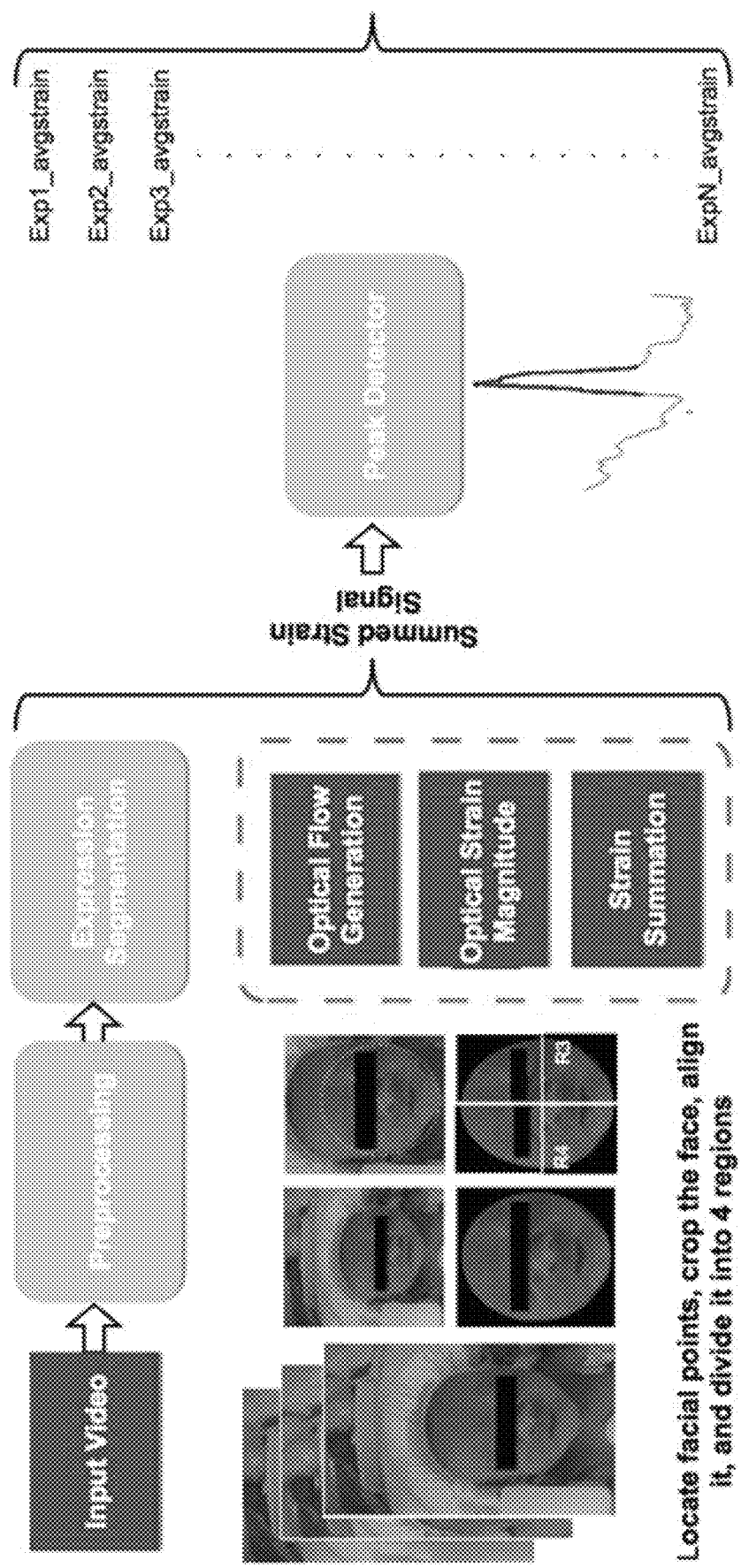
FIG. 8 is an overview of pain expression algorithm based on facial strain analysis, according to certain embodiments of the current invention.

FIG. 8 presents a block diagram of a segmentation algorithm. The results of applying this algorithm on video sequences of infants will become clearer as this specification continues.

The strain magnitude is a primary feature used to classify the expression as pain or no-pain. The expression-segmentation algorithm, described previously, generates a strain value for each frame of the segmented expression. A representative single strain value for the entire expression is then computed by taking the average of strain values over all frames of the expression. To classify the segmented expression, two classifiers—k Nearest-Neighbor (KNN) and support vector machine (SVM)—are employed.

Figure 7:
FIG. 7 is an illustration of the recording setup and equipment, according to certain embodiments of the current invention.

The segmentation algorithm is applied on a set of video sequences of the pain procedure to extract the strain magnitude value of each frame. The peak detector method then segments the expression by finding the points of maximum strain. Each of these segmented expressions is represented by a single strain value, as mentioned earlier. FIG. 7 shows the result of running the algorithm for an infant with acute pain. As can be seen in the figure, the algorithm does not generate continuous expression segmentation. This may happen because infants usually do not experience acute pain when the procedure starts by insertion of the lancet in the heel and instead, the acute pain occurs during the squeezing events.

Figure 3:
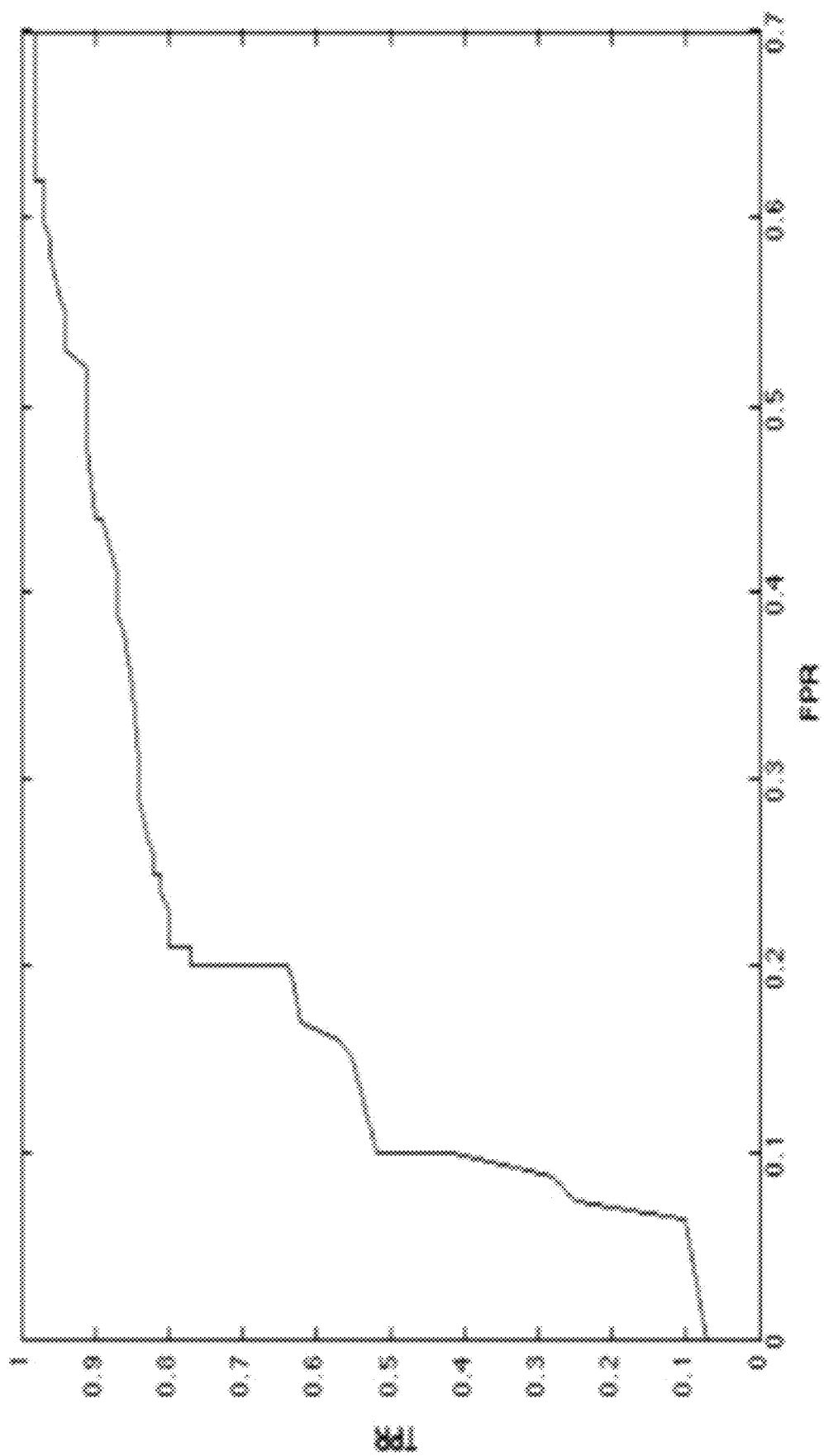
FIG. 3 is a graphical illustration depicting ROC curve of expression-spotting algorithm for 10 subjects. ROC achieves 80% TPR with 19% FPR.

The area under the Receiver Operating Characteristic curve (ROC) was adopted as a measure of performance for expression segmentation algorithm. The ROC, which is shown for 10 subjects in FIG. 3, achieves 80% True Positive Rate (TPR) with a 20% False Positive Rate (FPR), and has a peak of 97% TPR with less than 60% FPR. High FPR can be attributed to the segmentation algorithm classifying any facial motions (e.g., sucking on the pacifier) as expression.

Figure 4:
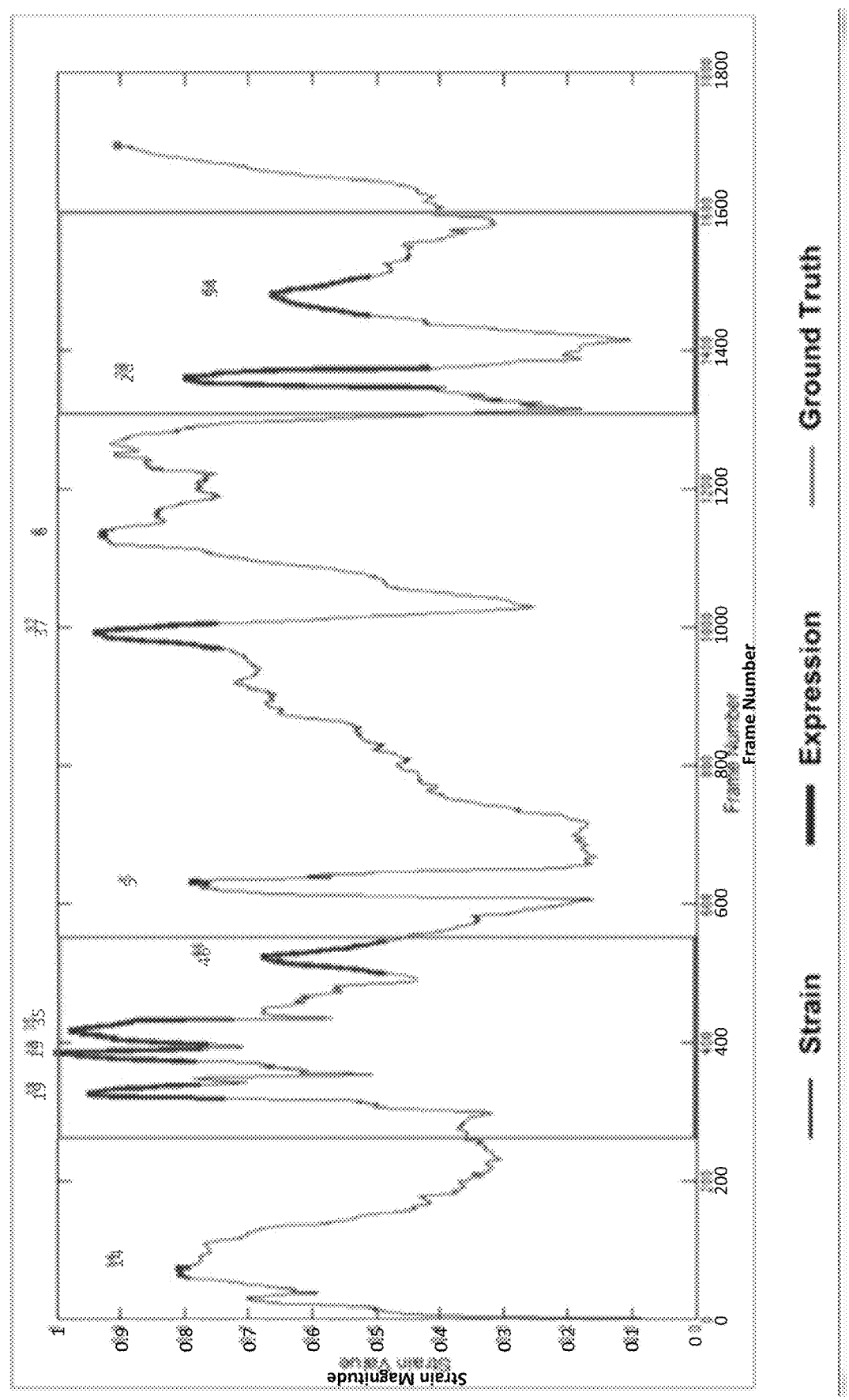
FIG. 4 is a graphical illustration depicting the results of expression segmentation testing. The accuracy of correctly recognizing the expression as pain for KNN and SVM classifiers was 96% and 94%, respectively. The blue line represents the strain value; the thick blue line represents the segmented expression; the number above the curve represents the number of frames that belong to the expression; and the red dashed line represents the start and end of the pain procedure.

As can be seen in FIG. 4, the algorithm segmented the infant's facial motion of sucking as expression. Alternatively, high FPR can be attributed to a failure in optical flow computation and strain estimation as a result of strong and out-of-plane head movements.

Video sequences of seven (7) subjects were used for training and videos of three subjects were used for testing (i.e., unseen data). For expression classification, KNN classifier in WEKA (Waikato Environment for Knowledge Analysis), which is JAVA machine learning software, was used with different values of k to classify the segmented expressions as pain or no-pain. The accuracy of the correctly classified instances was 96% with k=3. SVM (LIBSVM in WEKA) was also used for classification, and the accuracy for correctly classified instances was approximately 94%. This promising accuracy was obtained by utilizing the strain as a single feature for classification. Building a multi-class pain classifier by utilizing other features in addition to the strain is thus contemplated and described herein.

It is an object of certain embodiments of the current invention to develop a multimodal pain assessment system that aims to:
1. Monitor infants and detect signs that are associated with pain (e.g., pain expression, crying, body motion and vital signs) when the infants are left unattended; and
2. Generate a minimally biased total pain score based on several signs of pain and report this score to a nurse.

In application, this system can provide a consistent and minimally biased pain-scaling tool to be used in the NICU at hospitals, in houses as home-monitoring to check on an infant's condition at all hours, and in developing countries where there is a lack of medical workers/supplies.

It is contemplated herein that with larger datasets, other pain indicators, such as infants' crying, vital signs, and body motion can be utilized in addition to facial expressions. It should be noted that the results presented herein are based on the initial data collection, which has 10 subjects.

In an embodiment, the current invention is a machine-based infant pain assessment tool, which can monitor infants continuously, detect various pain indicators (e.g., facial expression of pain, crying, body motion and changes in heart rate), and generate a total pain score based on these indicators. The first step of the implementation of this tool has been accomplished by focusing on facial expression of pain as a behavioral indicator of pain, as described previously. As discussed, the model of recognizing infants' facial expression of pain has three main stages: infants' face detection and tracking, expression segmentation, and pain recognition.

Before analyzing facial expressions, the face is detected and tracked in video frames. There are several known face detection algorithms that can detect and track faces with high accuracy. However, as noted previously, most of these algorithms perform well in detecting adult faces, but fail in case of infants. In light of these difficulties, in certain embodiments of the current invention, the described infant face detection model was developed using the Adaptive Boosting algorithm, and the model was trained based on the dataset described herein. Other suitable face tracking algorithms may be used in the current invention as well.

The general steps performed to build the haar-cascade training model for analyzing infant facial expressions is described below. It is noted that this training model is an example implementation, and other known, suitable implementations for face tracking are contemplated by the current invention as well.

First, the image samples were prepared and were used to train the model. The image samples were divided into positive and negative image samples. Positive image samples contained the desired object to be detected, specifically the infants' faces here. Negative image samples were arbitrary images that did not contain the desired object (the infants' faces) to be detected. For example, 1,000 positive images containing infants' faces with different orientations were used, along with 2,000 negative images of the background without infants' faces.

Second, after preparing the images, the classifier was trained to distinguish between positive images (face) and negative images by building the haar-cascade classifier using C++ and Open CV. The classification learning process requires a set of positive and negative images for training, and a set of features (haar-like features) were selected using AdaBoost (adaptive boosting) for training the classifier. To improve the learning performance of the algorithm (which is sometimes called a weak learner), the AdaBoost algorithm can be used. AdaBoost provided guarantees in several procedures. The process of "boosting" works with the learning of single simple classifier and rewriting the weight of the data where errors were made with higher weights.

Afterwards, a second simple classifier was learned on the weighted classifier, and the data was re-weighted on the combination of the first and second classifier and so on until the final classifier was learned. Therefore, the final classifier was the combination of all previous n-classifiers. The AdaBoost cascade of classifiers was seen as a robust method of detection and characterization.

Finally, the trained model was tested using some unseen data (i.e. new images that were not used for training). The model outputs "1" and draws a rectangle around the detected region if it is a face, and outputs "0" if a face is not detected.

Matthew's algorithm was used to segment facial expression dynamically based on facial strain analysis. It should be noted here that Matthew's original work was evaluated with the six standard expressions (e.g., happiness, anger, disgust, surprise, fear, and sadness) and with the less challenging dataset of adults. The current algorithm was evaluated with a pain expression and with a more challenging dataset of infants.

Machine learning algorithms (e.g., support vector machine) were used to classify the segmented expression as pain expression (1) or other expressions (0).

Other pain indicators—for example infants' crying, vital signs, and body motion—can also be used to build a pain assessment tool with the ability to generate a total pain score based on various indicators, where each of these indicators generates a score that contributes to the total pain score.

To utilize an infant's crying as a pain indicator, a method was developed to recognize infants' emotions (e.g., pain, hunger) expressed in their crying based on frequency and pitch analysis of crying signals. The development of the method begins by performing preprocessing operations such as filtering out the noise and deciding the window size. Subsequently, frequency-based features, such as fast Fourier transform or Mel-frequency coefficients, are extracted to represent audio segments. These features are used subsequently to train and build a crying recognition classifier. Speech signal analysis is contemplated herein as well to recognize infants' emotions expressed in their crying.

Vital signs, including, but not limited to, heart rate, breathing rate, and oxygen saturation rate, measure the physical condition of an infant's body. For example, studies have shown that there is a strong correlation between an infant's pain intensity and an increase in the infant's heart rate. A method was developed herein to analyze sequences of vital signs and determine whether a specific sequence correlates to pain based on score function. For example, to predict whether a sequence of heart rate corresponds to pain, a score for each frame in the sequence is generated, and the sum of these scores gives a total score for the entire sequence. This total score corresponds to pain if it exceeds a predetermined threshold. Other parametric and non-parametric classifiers are contemplated herein and may also be used to quantify and score vital signs.

Infants tend to move their arms and/or legs when they experience pain. Thus, it may also be important to utilize infants' body motion as pain indicator. The infants' motions are analyzed and used to detect motions corresponding to pain.

As contemplated herein, the instant pain score generator system/methodology/software uses image/video processing and machine learning algorithms to generate both individual pain assessment scores for each parameter and also an overall total pain score, which is a summation and/or weighted balance of the individual pain assessment scores. The generator can be integrated into the infant's incubator system or to a camera or installed as an application in an electronic device such as a smartphone or tablet. The resulting infant's pain assessment tool measures an infant's pain intensity using various indicators, such as facial expression, crying, body motion and vital signs, as described previously.

Figure 6:
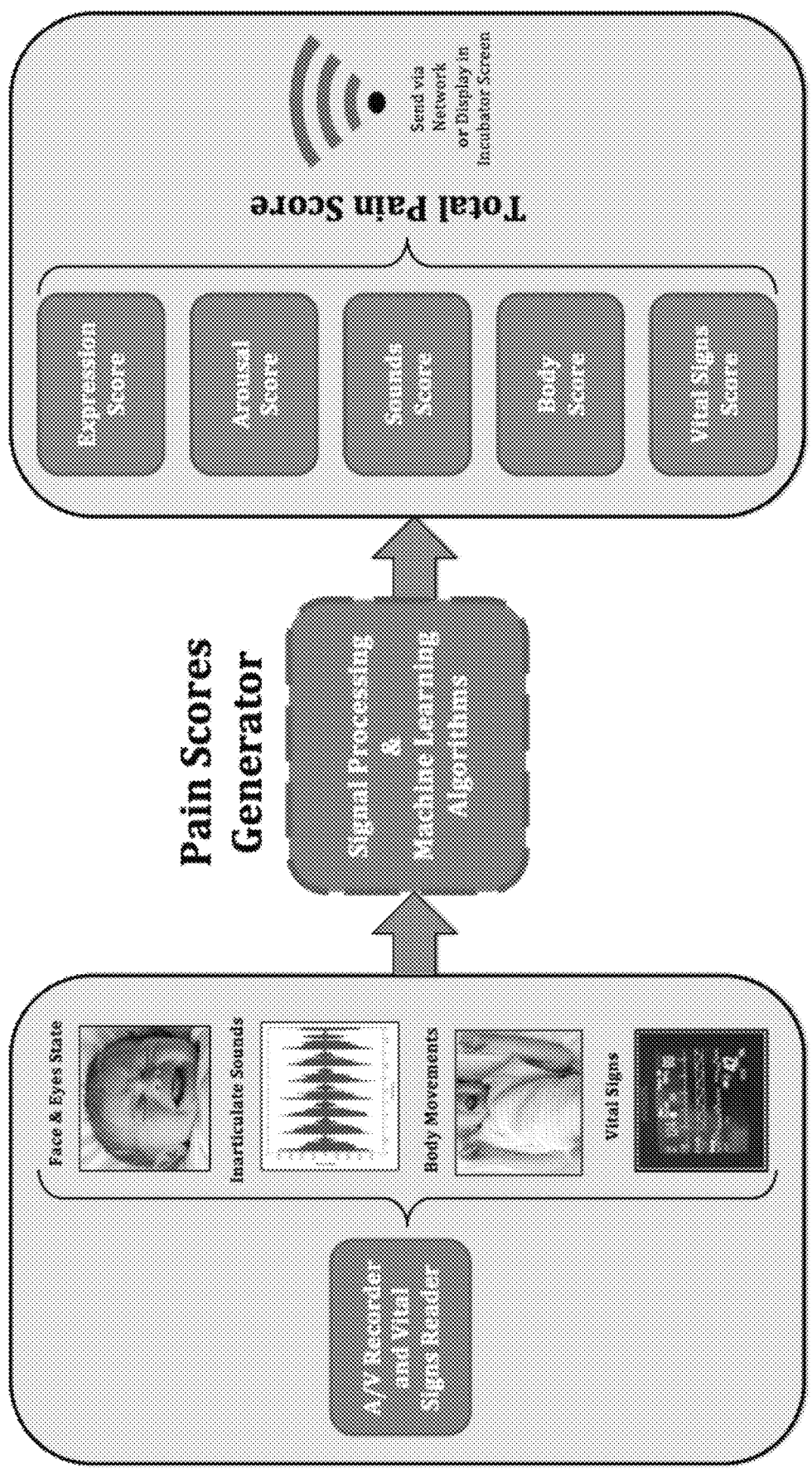
FIG. 6 is an image depicting the components of the infants' pain assessment tool which uses different measures to determine a total pain score. In use, data is acquired of different pain indicators using video, audio, body and vital signs recording. Software is used to process and analyze the acquired data and generate a total pain score by summing up all of the pain scores from the various pain indicators. The generated total pain score is then sent to a remote station via Wi-Fi or alternatively it is displayed in the infant's incubator.

The components of the infant's pain assessment tool are illustrated in FIG. 6. In use, the infant's pain assessment tool employs data readers, for example cameras, microphones or other recorders, to obtain infant data of various pain indicators such as facial expressions, voice, vital signs, and body motion. The data reader can be attached to the incubator itself or to a stand adjacent to or otherwise corresponding to the incubator.

A total or weighted pain score is generated based on the various indicators by utilizing several signal and image/video processing and machine learning algorithms, such as optical flow, facial strain, local binary patterns (LBP), linear predictive coding (LPC), linear regression, neural network, etc. Machine learning classifiers or algorithms were divided into two main categories: parametric (linear regression) and non-parametric (neural network). The total/weighted pain score is computed by weighing or summing up a variety of pain scores—such as score of pain expression, score of crying, score of body motion, score of vital signs, and score of state of arousal—though additional suitable categories are contemplated herein as well.

Table II below illustrates five (5) different pain scores. Pain generator software/code can be integrated into the infant's incubator, a camera, etc.

TABLE II

| | NPASS (Neonatal Pain, Agitation, Sedation Scale) | | | | |
|---|---|---|---|---|---|
| Assessment | Sedation | | Normal | Pain/Agitation | |
| Criteria | −2 | −1 | 0 | 1 | 2 |
| Crying Irritability | No cry with painful stimuli | Moans or cries minimally with painful stimuli | Appropriate crying Not irritable | Irritable or crying at intervals Consolable | High-pitched or silent-continuous cry Inconsolable |
| Behavior State | No arousal to any stimuli No spontaneous movement | Arouses minimally to stimuli Little spontaneous movement | Appropriate for gestational age | Restless, squirming Awakens frequently | Arching, kicking Constantly awake OR Arouses minimally/no movement (not sedated) |
| Facial Expression | Mouth is lax No expression | Minimal expression with stimuli | Relaxed Appropriate | Any pain expression intermittent | Any pain expression continual |
| Extremities Tone | No grasp reflex Flaccid tone | Weak grasp reflex ↓ muscle tone | Relaxed hands and feet Normal tone | Intermittent clenched toes, fists, or finger splay Body is not tense | Continual clenched toes, fists, or finger splay Body is tense |
| Vital Signs HR, RR, BP, SaO$_2$ | No variability with stimuli Hypoventilation or apnea | <10% variability from baseline with stimuli | Within baseline or normal for gestational age | ↑ 10-20% from baseline SaO$_2$ 76-85% with stimulation-quick recovery ↑ | ↑ >20% from baseline SaO$_2$ ≤ 75% with stimulation-slow recovery ↑ Out of sync with vent |

Adding up the score for each parameter, for example, generates a total pain score. The breathing pattern parameter corresponds to the vital signs, and the arms/legs parameter corresponds to body motion.

After the total pain score is generated, the score can be transmitted wirelessly (e.g., Wi-Fi) to a remote station (e.g. a nurse's station, doctor's station, caregiver's smart device, etc.) or can be displayed on the infant's incubator itself.

Video and audio data (i.e., video data of face, body, and sounds) along with vital signs data for a total of 43 subjects older than 30 weeks gestational age (e.g., premature and infants) were recorded using cameras (e.g., GOPRO cameras) under two different pain conditions: acute and chronic. Gestational age was calculated from the first day of the mother's last menstrual period. Acute pain recordings were carried out during heel lancing procedures that were previously scheduled for routine blood test in the presence of nurses who scored the pain moments using the NIPS (Neonatal Infant Pain Scale) scoring tool. The scores were taken prior to, at the start, and during the procedure, and at every minute after the completion of the procedure for around five minutes. These scores were used as ground-truth, to validate the results of the instant system and methodology. Infants with chronic pain were monitored during the post-operative recovery for up to three (3) hours in the presence of nurses who scored the pain using the NPASS (Neonatal Pain, Agitation, Sedation Scale) scoring tool prior the surgery (i.e., normal state), and every 15 minutes after the surgery and during the chronic pain.

Forty-three infants, older than 30 weeks gestational age (e.g., premature and newborn), were videotaped in the NICU at Tampa General Hospital. Exclusion criteria included infants with facial abnormality or gestational age less than 30 weeks. Prior to data collection, informed consent was obtained from each infant's parents. The procedure for collecting the data complied with the protocols and ethical directives for research involving human subjects at the University of South Florida.

The average age of the recorded infants was around 37 weeks gestational age (min: 30 weeks, max: 41 weeks). Thirty infants were non-Hispanic, and 13 infants were Hispanic. Infants were recorded under two different pain conditions: acute and chronic pain. Thirty-four infants were recorded during acute pain procedure, seven infants were recorded during both chronic pain and acute pain, and two infants were recorded during chronic pain procedure. Acute pain recordings were carried out during immunization or heel sticking procedure, which had been previously scheduled for routine blood test. The infants with chronic pain were recorded during the post-operative recovery for up to 3 hours in the presence of nurses who monitored the infants and scored his/her pain experience.

Prior to data collection, the study was explained to each infant's parents, and their permission was obtained by asking them to sign a consent form. Thereafter, the recording equipment—which included cameras (e.g., GOPRO), camera stands, vital signs reader, tablet (e.g., IPAD MINI), subject's identifier sheet, and the scoring sheets—were prepared and brought to the infant's room. Infants were recorded with the cameras at high (e.g., 4K) resolution. The recorded data included video sequences of the infant's face/upper body, audio data of the infant's voice, and data pertaining to the infant's vital signs. Any suitable vital signs reader, such MEDTRONIC VITAL SYNC Virtual Patient Monitoring Platform, can be used for recording a wide range of vital signs data.

The acute pain recording (e.g., immunization or heel-sticking) started by recording the infant for about five (5) minutes in normal state before the pain procedure, during the procedure, and for about (5) minutes after the completion of the procedure in the presence of expert nurses who scored moments of pain. For the chronic pain (e.g., post-operative pain), infants were recorded first in normal state prior the surgery and then after the surgery for up to about three (3) hours in the presence of expert nurses who scored moments of pain.

Two nurses attended the recordings and filled out the ground truth sheets using NIPS (Neonatal Infant Pain Scale) (Table III) and NPASS (Neonatal Pain, Agitation, Sedation Scale) (Table II) pain scales. NIPS is used to scale the acute pain and NPASS is used to scale the chronic pain. The NIPS pain scale has binary ranges for all indicators except crying. The NPASS pain scale ranges from −2 to 2.

TABLE III

NIPS Pain Scale (Neonatal Infant Pain Scale). A sum of the points is obtained.

| Parameter | Finding | Points |
| --- | --- | --- |
| Facial Expression | Relaxed | 0 |
| | Grimace | 1 |
| Cry | No cry | 0 |
| | Whimper | 1 |
| | Vigorous crying | 2 |
| Breathing Pattern | Relaxed | 0 |
| | Change in breathing | 1 |
| Arms | Relaxed | 0 |
| | Flexed/extended | 1 |
| Legs | Relaxed | 0 |
| | Flexed/extended | 1 |
| State of Arousal | Sleeping/awake | 0 |
| | Fussy | 1 |

Expert nurses in two (2) different conditions, the initial real-life scores and the short-video episodes scores, took the ground truth scores by rating the infant pain experience. A nurse, who attends the pain procedure and observes signs of pain, fills out the initial scores. Each acute recording has a total of 7 ground truth scores, which were collected prior to the pain procedure, at the start of pain procedure, and at every minute for around five (5) minutes after the pain procedure is completed. The ground truth for the chronic pain was taken every fifteen (15) minutes prior the surgery in the normal state and every fifteen (15) minutes after the surgery and during the chronic pain.

For short-video episodes, four expert nurses watched these videos of the pain procedure individually and scored them. The length of video episodes was five (5) seconds and ten (10) seconds for acute pain and chronic pain, respectively.

Experiments are conducted to measure the subjectivity of pain scores between different observers. For examples, differences between an observer's initial scores and the same observer's video episodes scores or the variability of ground truth scores among four different observers.

This dataset is challenging because infants tend to make unpredictable movements (i.e. infants make different and strong out-of-plane head movements). In addition, self-occlusion by hand or occlusion by external items such as a pacifier, toys, or tapes make the dataset challenging as well as low lighting conditions.

As discussed herein, an embodiment of the current invention is a multimodal computer-aided pain assessment tool for use in preterm and term infants. While the prior art demonstrated the relationship between isolated behavioral and physiologic changes and infant pain, a pain assessment tool is needed that allows for the automated integration of infants' facial strain patterns, body motion, crying sounds, and vital signs. This pain assessment tool is enabled herein. This integrated data (infants' facial strain patterns, body motion, crying sounds, and vital signs) was evaluated in comparison with validated nurse-generated pain scores to perform multivariate regression analysis and establish pain inference models that can assess pain using the identified indicators.

An objective is to demonstrate that computer-aided pain assessment provides a sensitive and consistent assessment of infant pain similar to the traditional nurse scoring. The computer-aided pain assessment is accomplished with a cost-effective system based on video cameras and image/signal processing algorithms. This diagnostic tool improves the assessment of pain in infants and helps guide treatment by generating a more consistent and objective pain assessment.

Preliminary studies on premature and term infants were performed in the NICU at Tampa General Hospital (TGH). The procedure of collecting the data complied with the protocols and ethical directives for research involving human subjects. A total of 43 infants were videotaped during acute episodic and prolonged acute painful procedures. Prior to video recording, informed consent was taken from the infant's parents. FIG. 7 is an illustration of the recording setup and equipment.

For the acute episodic pain assessments, thirty-four infants were videotaped during brief skin lancing procedure (e.g., heel lancing and immunization) in the presence of two trained nurses who assessed their pain using the NIPS pain scale. The infants were recorded for five minutes prior the procedure to determine their baseline state of arousal and pre-procedure NIPS score. The NIPS score was documented again at the start of the procedure and then every minute for five minutes after the procedure was completed. NIPS assessments were time stamped on the recorded video for synchronization with the automated scores.

For the prolonged acute pain assessments, a total of nine (9) infants were recorded during the post-operative period (laparotomy, gastrostomy tube placement) for approximately three (3) hours in the presence of two trained nurses. The nurses assessed the infants using NPASS pain scale at the start of the recording after observing the infant and then every 15 minutes during the evaluation period. NPASS assessments were time stamped on the recorded video for synchronization with the automated scores.

Based on the initial data collection, a novel process was developed for assessing infant pain on video sequences by utilizing infants' facial expressions. This methodology includes three main stages: (1) detection of the infant's face in a video sequence followed by preprocessing operations including face alignment; (2) expression segmentation based on facial strain analysis; and (3) expression recognition and classification. Manual detection of infants' faces was performed to extract facial points. A strain algorithm was employed to segment expressions by exploiting the non-rigid facial motion that occurs during facial expression; FIG. 8 presents an overview of this methodology. The accuracy of classifying the segmented expressions as pain or no pain using k Nearest Neighbor (KNN) and support vector machine (SVM) were 96% and 94%, respectively.

Table IV shows the confusion matrix of a KNN classifier. The confusion matrix, which is used to measure the classifier's performance, is a matrix that has information about the actual (column) and predicated (row) classifications acquired by a specific classifier. The results of the current methodology indicate that dynamic analysis of facial expression in infants can be used to assess pain.

TABLE IV

Confusion Matrix of KNN. N represents the total number of instances. The first row of the matrix represents the predicted class and the first column represents the class of actual ground truth. For instance, the KNN classifier was able to correctly classify 28 pain instances as pain and misclassify one instance of pain as no pain.

| | | Classifier Prediction | | |
|---|---|---|---|---|
| N = 67 | | Pain | No Pain | Total |
| Ground Truth (Actual) | Pain | 28 | 1 | 29 |
| | No Pain | 2 | 36 | 38 |

Figure 9:
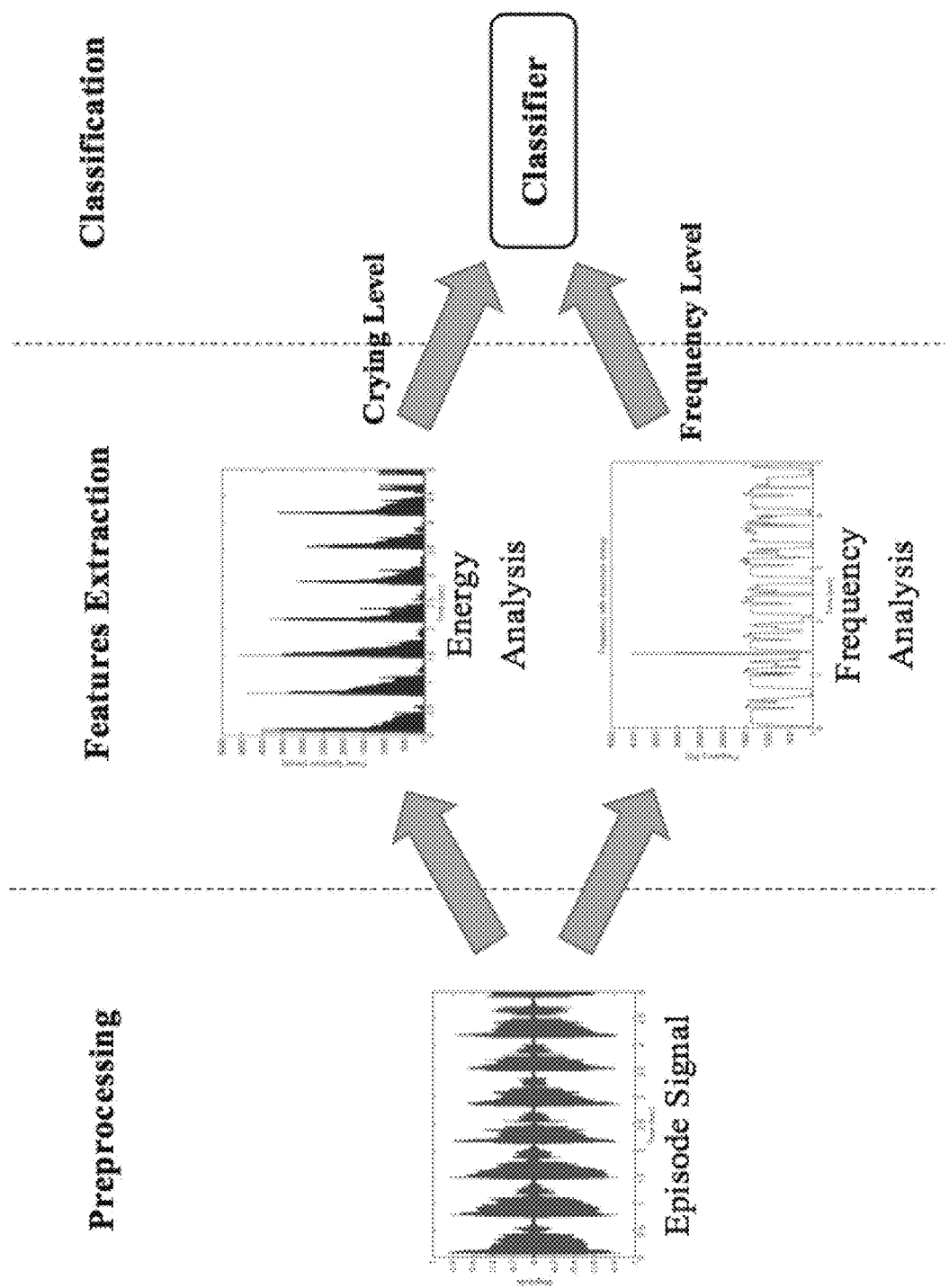
FIG. 9 is an illustration of the pain detection method based on infants' sounds analysis, according to certain embodiments of the current invention.

To classify infant crying as it pertains to infant pain, a method was developed and includes three main stages: preprocessing stage, features extraction stage, and classification stage. In the preprocessing stage, the entire audio signal is segmented into pain/no-pain episodes based on the given ground truth. In the feature extraction stage, a set of features (e.g., crying level and frequency level) is extracted from the segmented episodes based on energy and frequency analysis. In the classification stage, the extracted features of each episode are classified into one of three classes: no cry (class 0), whimper (class 1), and vigorous crying (class 2). The accuracy of classifying the crying sounds based on simple thresholding was approximately 88%. FIG. 9 illustrates the stages of this method, and Table V shows the confusion matrix of the classification stage.

TABLE V

Confusion Matrix.

| | | Classifier Prediction | | | |
|---|---|---|---|---|---|
| | N = 49 | Class 0 | Class 1 | Class 2 | |
| Ground Truth (Actual) | Class 0 | 34 | 2 | 0 | 36 |
| | Class 1 | 0 | 3 | 1 | 4 |
| | Class 2 | 1 | 2 | 6 | 9 |

Vital signs measurements have been collected in the current study for infants under different pain characteristics (i.e., isolated and prolonged acute pain). Specifically, vital signs data (i.e., heart rate (HR), respiratory rate (RR), and oxygen saturation ($SpO_2$)) for a total of 18 infants were collected to ascertain the correlation between these measurements and infants' pain experience using machine-learning algorithms.

Figure 10:
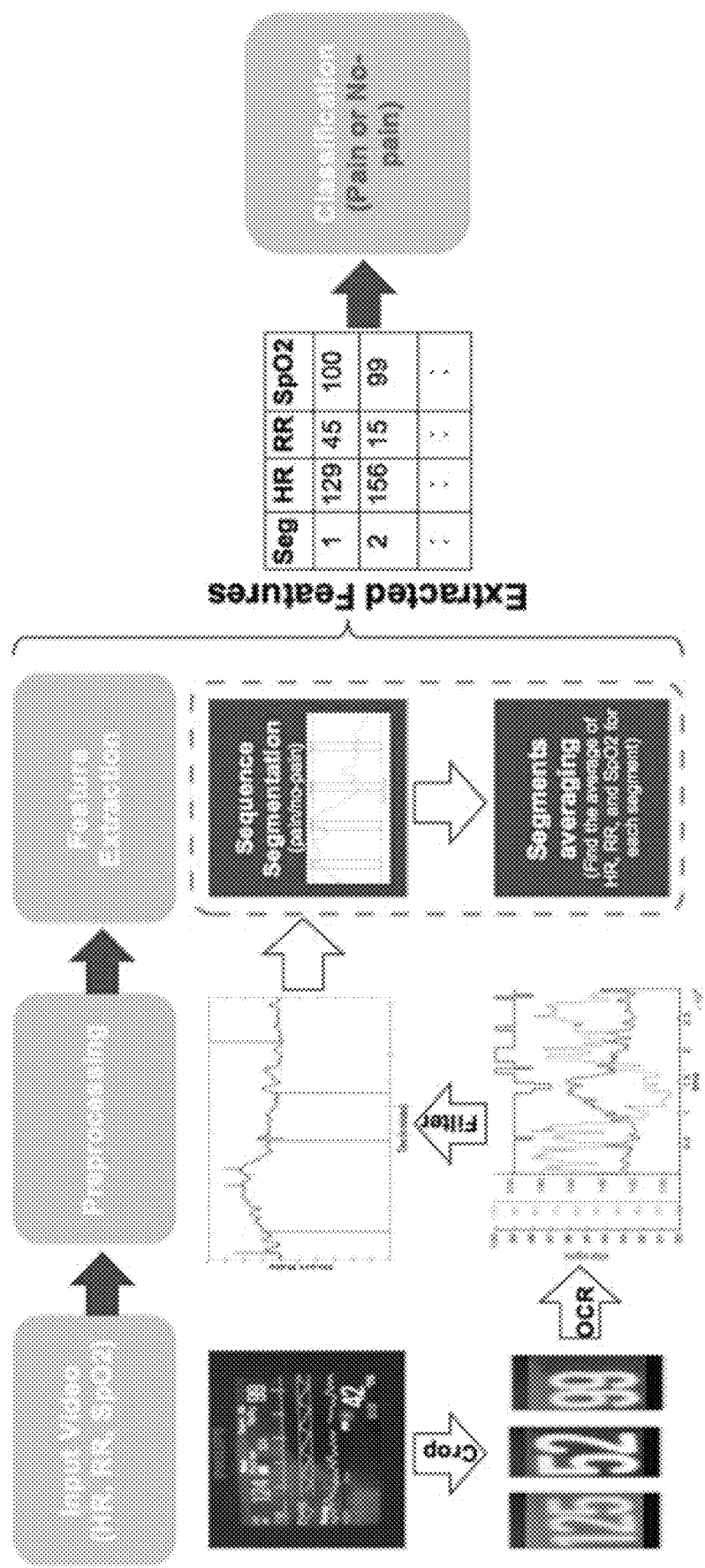
FIG. 10 is an illustration of the pain detection method based on infants' vital signs analysis, according to certain embodiments of the current invention.

The method to assess infant pain based on vital signs analysis includes three main stages: preprocessing stage, feature extraction stage, and classification stage. In the preprocessing stage, in which optical character recognition (OCR) is performed, the videotaped vital signs frames are transferred into sequences of digital numbers; a median filter is then applied to these sequences to exclude the outliers. In the feature extraction stage, the filtered sequences are segmented into pain/no-pain episodes based on the given ground truth. The features of each episode are then extracted by taking the average of that episode. In other words, three features (HR, RR, and $SpO_2$) were extracted for each episode. In the classification stage, the extracted features are classified as pain (1) or no-pain (0) by utilizing different machine learning classifiers; the accuracy of classifying this stage based on tree classifier (i.e., random forest) was found to be about 97% (accuracy was increased by extracting the outliers instances and applying more than one trees (forest of trees)). A depiction of these three stages is presented in FIG. 10, and Table VI shows the confusion matrix.

TABLE VI

Confusion matrix.

|  | Pain | No-pain |
|---|---|---|
| Pain | 65 | 0 |
| No-pain | 4 | 61 |

The infants' body motions may also correspond to pain and can be measured by applying well-known motions estimation algorithms, such as optical flow, block matching, and pixel tracking algorithms.

Correlating pain with the infant's state of arousal is also contemplated herein. State of arousal is defined as the state of being fussy or relaxed during pain stimuli. The score of this indicator is given by observing the eyes motion (e.g., eyes continually shut or open), speed of the breathing, and arms motions). Several eye-blinking detections and arms motions algorithms, along with the speed of infant breathing, can be applied to automate this process.

Figure 11:
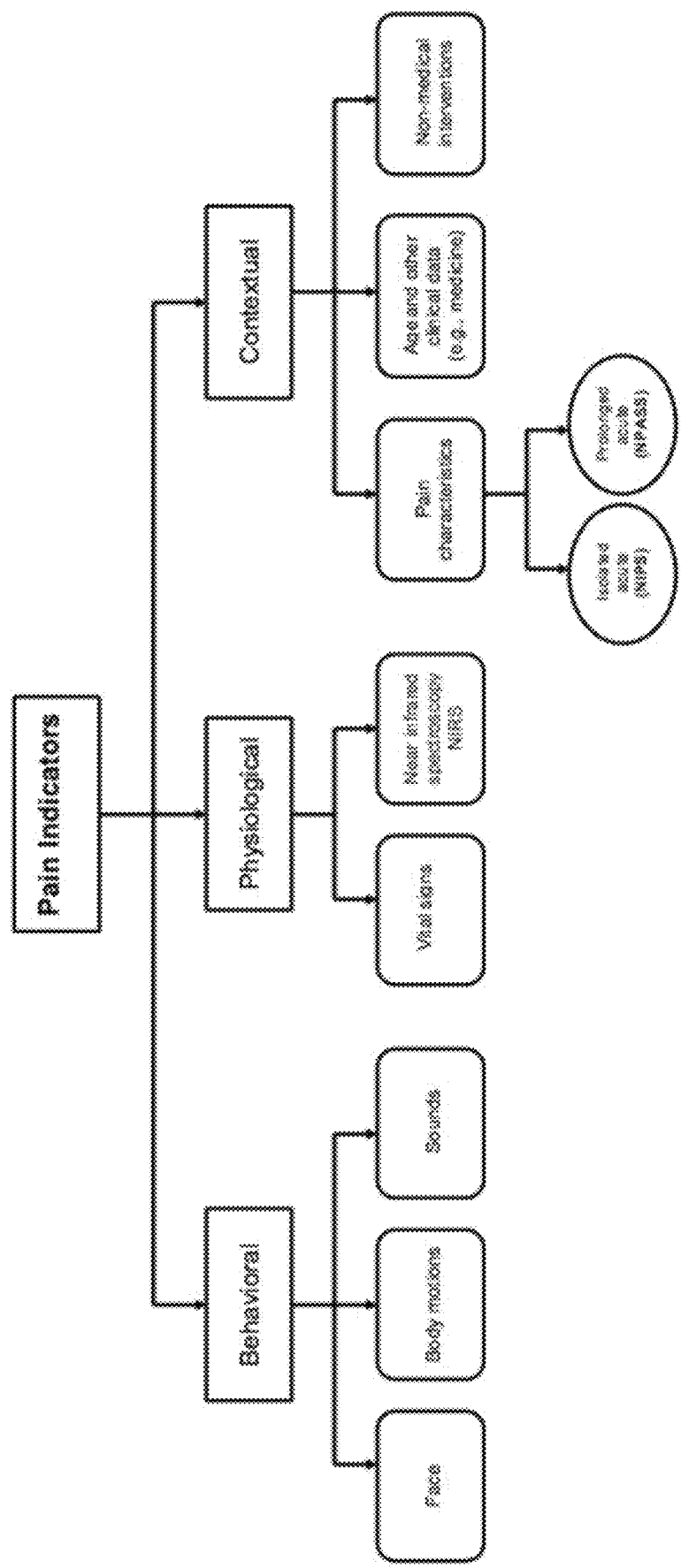
FIG. 11 is a diagram of the pain indicators, according to certain embodiments of the current invention.
Figure 13:
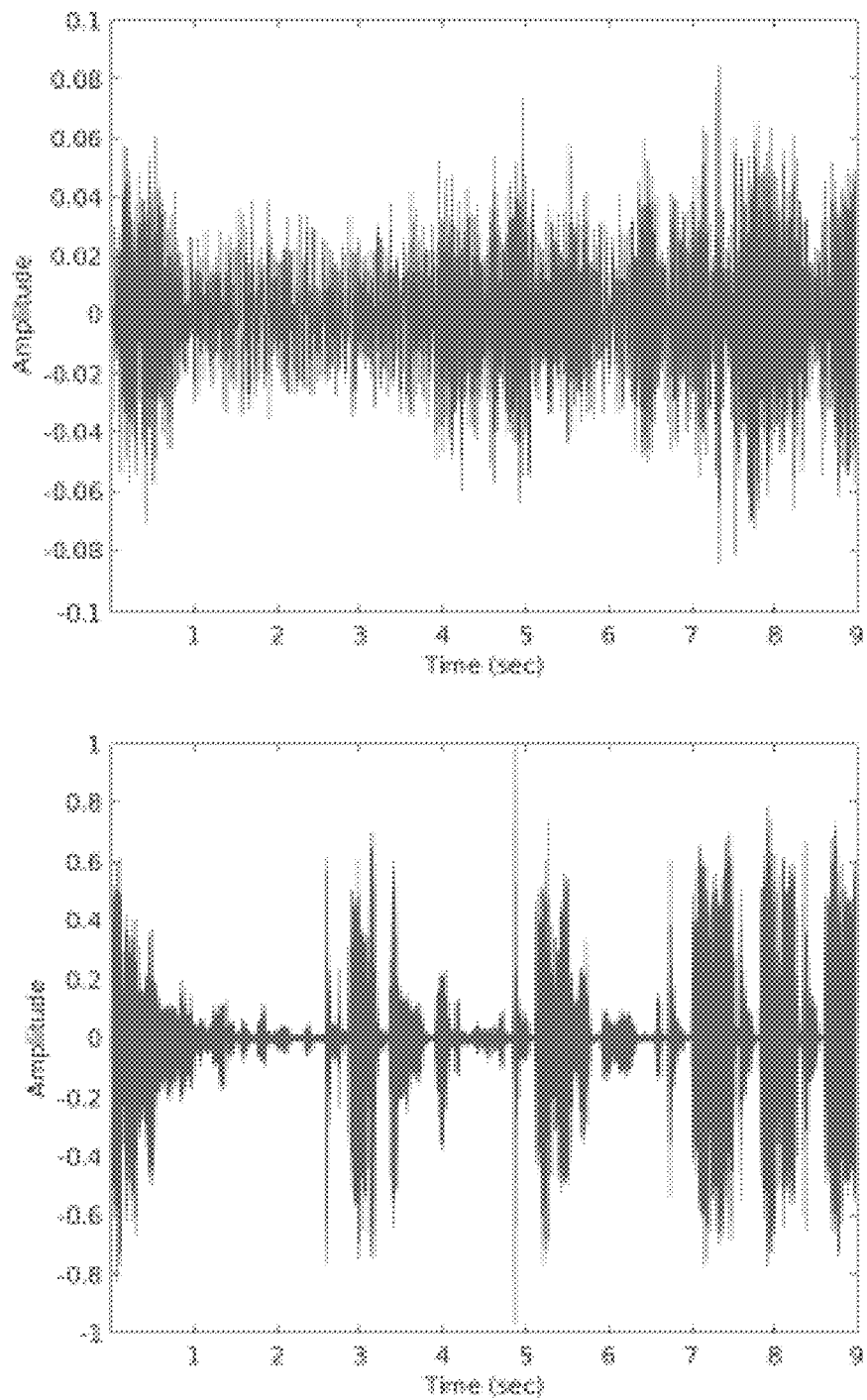
FIG. 13 is an illustration of audio signals from procedural (top) and postoperative (bottom) pain. In both cases, the pain score of crying is 2 at a sample rate of 44.1 kHz.

An objective of the invention is to build an automated infant pain assessment system that simulates the nurses' task in assessing infant pain at the NICU. Specifically, this system includes a tool that monitors infants and observes signs of pain by taking into account various pain indicators, as seen in FIG. 11.

A behavioral indicator is considered and includes the following:
  Facial pain indicators such as lowered brows, tightly closed eyes, opened mouth, raised cheeks, and broadened nose.
  Body motion pain indicators such as flexed or extended arms/legs, diffuse squirm, finger splay, stretch/drown, grasping, hand in mouth, and fisting.
  Sounds such as whimper, moans, and high-pitched crying.
A physiological is considered and includes the following:
  Vital signs such as heart rate (HR), respiratory rate and pattern (RR), saturation rate ($SpO_2$), and the blood pressure (BP).
  Near infrared spectroscopy (NIRS) readings.
A contextual indicator is considered and includes the following:
  Pain characteristics such as isolated acute pain and prolonged acute pain. Each of these pain types has different measurements and pain scales; thus, this parameter can be used to partition the pain assessment system into two different pain models: isolated acute pain model and prolonged acute pain model.
  Gestational age (GA) and day of life age. This indicator may be important since the infants' reaction to pain procedures can vary based on their age.
  Clinical data such as medication type and dose, weight/length, race/ethnicity, and gender.
  Non-medical interventions such as the mother's presence, rubbing, and the pacifier.

Several studies have found associations between the infants' age and their reaction to pain; the most premature infants have limited ability to behaviorally or physiologically respond to painful procedures. Thus, extra points can be added to their pain score, based on their gestational age, as compensation for their limitation. Due to this fact, the infants (i.e., samples) can be grouped into four different groups based on their gestational age; these groups, as mentioned above, should be isolated and treated separately.

To develop a system that has the ability to assess pain for different infants' population, the automated infant pain assessment system can be partitioned into two different models based on the pain characteristics: isolated acute pain model and prolonged acute pain model. Each of these models can have its own pain scale and four different groups generated based on infants' group. Both the isolated and prolonged acute pain models can be formulated mathematically as a multivariable regression model. The box diagrams in FIGS. 12A-12B provide a mathematical formulation of these pain models. As can be seen, $X_{1:5}$ represents the feature vectors for each of the pain indicators (i.e., predictors of the regression model). Each of these vectors has its own weight that varies from one group to another based on the infant age. For instance, infants of Group 1 may have difficulty expressing their pain through behavioral pain indictor; more weight should be added in this case to physiological pain indictors. Finally, the total pain score $Y_p$, which represents the response value of the regression model, is used to assess the pain by comparing $Y_p$ to a predetermined threshold. If the total pain score exceeds the given/predetermined threshold, a corresponding therapy or intervention is indicated by the system.

Figure 14:
FIG. 14 illustrates photographic examples from neonatal procedural (left) and postoperative (right) pain. In both cases, the score of facial expression is 1.

In addition to providing a total pain score, the present invention addresses the need for a multimodal spatiotemporal deep learning approach for neonatal postoperative pain assessment. FIG. 1 and FIG. 14 present examples of crying sounds and facial expressions captured during procedural and postoperative pain, respectively. As can be seen, postoperative pain is less intense and occurs at different time intervals as compared to procedural pain (e.g., heel lancing). Hence, it is believed that assessing postoperative pain frequently and consistently is critical for the development of effective plans for interventions.

The current practice for pain assessment using multidimensional score-based scales is discontinuous, inconsistent and suffers from high inter-observer and intra-observer variations. To mitigate these limitations, several artificial intelligence-based methods have been published in the literature. However, few of the known method focus on assessing postoperative pain.

While the previously described invention method provides a multimodal approach for assessing procedural acute pain using handcrafted methods, it does not integrate temporal information. In the embodiments described below, a spatiotemporal and multimodal AI-based approach is proposed for assessing neonatal postoperative pain.

VGG-Net is a state-of-the-art Convolutional Neural Network (CNN) for visual feature extraction. Although several versions of VGG-Net exist, VGG-16 has been widely and successfully used. VGG-16 consists of 13 uniform convolution layers followed by 3 fully connected layers. Each convolution layer uses a 3.3 kernel-size filters and is followed by a pooling layer. The network starts with 64 depth and gradually increases by a factor of 2 until it reaches 512. The depth of the network and the use of small kernel size allow for the extraction of robust visual features. In the present invention, VGG-16 network is used to extract visual features from the face, body, and spectrogram images of sounds.

Long Short Term Memory (LSTM) is one type of Recurrent Current Neural Networks (RNN) that is capable of learning the temporal information in a given sequence. Although RNN can handle long-term dependencies in theory, these networks fail to learn these dependencies in practice. To solve this issue, LSTM network was introduced and has been widely used in a wide range of applications.

LSTM solves the long-term dependencies as well as vanishing gradient problem using the cell state, which is controlled by three gates: input, forget, and output gates. The input gate controls which information should be saved to the cell state. The forget gate controls which information should be ignored or forgotten from the previous cell state. Finally, the output gate controls which information should be sent to the next state. In the spatiotemporal embodiments of the present invention, LSTM is used with the deep features, extracted by VGG-Net, to learn the temporal pattern and dynamics of postoperative pain.

Bilinear CNN is introduced to address fine-grained image classification. It uses two CNN streams to extract features from two different regions of the same image, and the final bilinear vector is generated by combining the features of the two CNN streams. Mathematically, given that there are two CNN streams X and Y with pooling layer P and classification layer C, then the bilinear model can be represented as B=(X, Y, P, C). Now for a location L within the image I, if the feature functions are FX and FY, then the bilinear feature vector b, can be represented as follows.

$$b = (I, L, F_X, F_Y) \rightarrow F_X(I,L)^T F_Y(I,L)$$

Finally, a sum-pooling is applied to collect all the bilinear features from the entire image.

To improve the performance, the final bilinear vector u=Σb(l, L) is forwarded to the following steps.

$$v \xleftarrow{sqrt} (\text{sign}(u) * \sqrt{|u|})$$

$$w \xleftarrow{normalization} (v/\|v\|_2)$$

The bilinear feature vector extracts orderless features, which provide better texture representation as compared to the orderfull features in the fine-grained image classification problem. This network is capable of extracting robust features in the context of the different pose, lighting and background. This resembles the context of the real-world NICU environment. In various embodiments of the invention, two VGG-16 models were used as CNN streams of the Bilinear CNN.

To evaluate the temporal multimodal approach of the present invention, a dataset containing data of procedural (acute) and postoperative (acute prolonged) neonatal pain was used. The dataset, which is known as USF-MNPAD-I (University of South Florida Multimodal Neonatal Pain Assessment Dataset), was collected at the NICU in Tampa General Hospital, Fla., USA. The dataset consists of 45 neonates with a gestational age that ranges from 30 to 41 weeks. It has ethnically and racially diverse population including Asian, African American, and Caucasian neonates. The data collection was approved by the USF Ethics Review Board (IRB #Pro00014318)

USF-MNPAD-I dataset has video, audio, and physiological data. To collect the video and audio data, a Go-Pro Hero Black 5 camera was used. The camera was set up on a camera stand facing the infant's incubator to capture the neonate's face and body. A bedside vital sign Phillips MP-70 monitor was used to collect the physiological data including heart rate, blood pressure, and oxygen saturation. All these data were recorded from neonates experiencing either short-term procedural or postoperative pan during their NICU hospitalization. The dataset contains multimodal data for 36 neonates (17 female) recorded during baseline, during a procedural pain stimulus (i.e., heel lancing and immunization), and immediately after the completion of the stimulus. In case of postoperative pain, 9 neonates (5 males) were recorded prior to major surgery (e.g., omphalocele-repair) to get their baseline state and monitored for three hours after the surgery to get their postoperative pain state. Note that in the current dataset, the neonates were monitored only up to three hours after the surgery due to clinical constraints.

The ground truth labels for both types of pain were documented independently by trained nurses using NIPS (Neonatal Infant Pain Scale) and N-PASS (Neonatal Pain, Agitation and Sedation Scale) for procedural and postoperative pain, respectively. NIPS score-based pain scale has a total pain score that ranges from 0 to 7, and three levels of pain: no-pain (total score of 0-2), moderate pain (total score of 3-4), and severe pain (total score >4). The final score is generated by summing the individual scores of the following pain indicators: facial expression (score of 0 or 1), crying sound (score of 0, 1, or 2), breathing patterns (score of 0 or 1), arms movement (score of 0 or 1), legs movement (score of 0 or 1), and state of arousal (score of 0 or 1). N-PASS score-based pain scale has a total score that ranges from −10 to +10, and five levels: deep sedation (score −10 to −5), light sedation (score −5 to −2), normal (score 0-2), moderate pain (score 3-5), and severe pain (score >5). This total score is generated by summing the individual scores of the following pain indicators: crying irritability, behavior state, facial expression, extremities of tone, and vital signs (heart rate, blood pressure, oxygen saturation). Each of these indicators has a score that ranges from −2 to +2, where minus (−), 0, and plus (+) indicate the sedation, normal, and pain states, respectively. In the dataset, there are 109, 33, and 76 samples for normal state, moderate pain, and severe pain, respectively.

Figure 15:
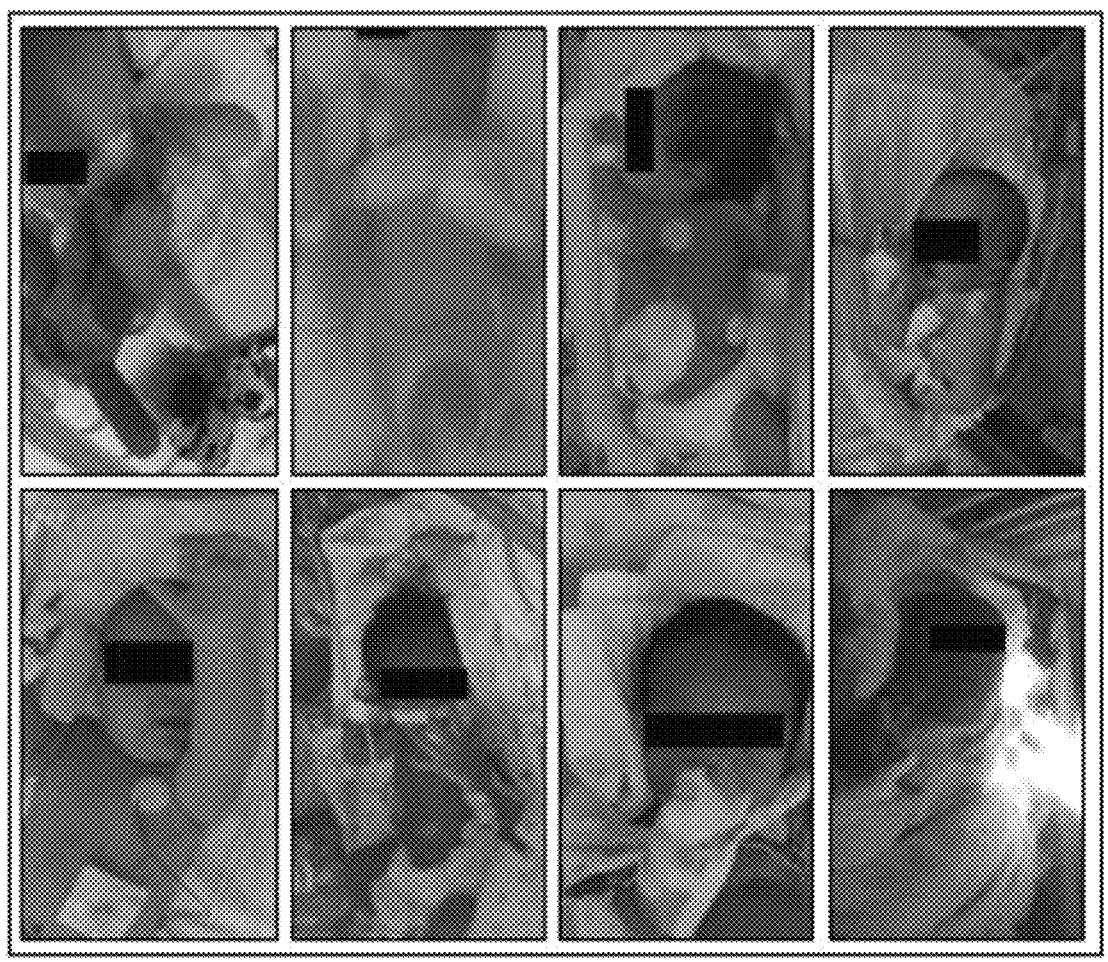
FIG. 15 illustrates photographic examples from real-world neonatal postoperative dataset.

The dataset was labeled manually by independent trained nurses. The agreement between the nurses is measured using Kappa coefficient (0.85) and Pearson correlation (0.89). All the cases of agreement were included, and the cases of disagreement were excluded from further analysis. FIG. 15 shows examples from neonates recorded during postoperative pain. The images were randomly selected and masked to ensure confidentiality.

Figure 16:
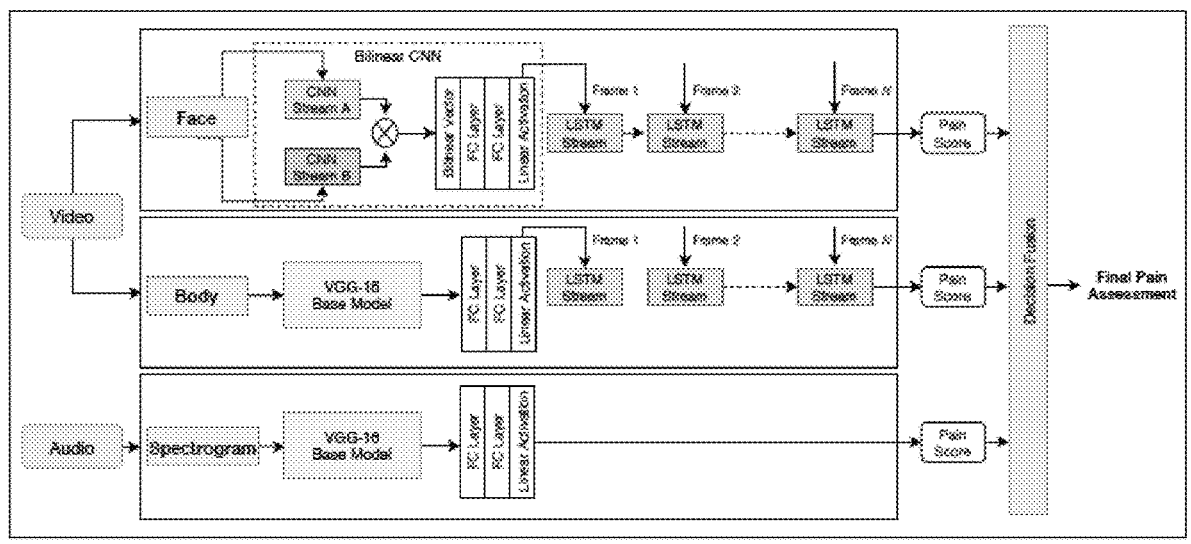
FIG. 16 is a flow diagram illustrating the proposed spatiotemporal multimodal approach for neonatal postoperative pain assessment, in accordance with an embodiment of the present invention.
Figure 17:
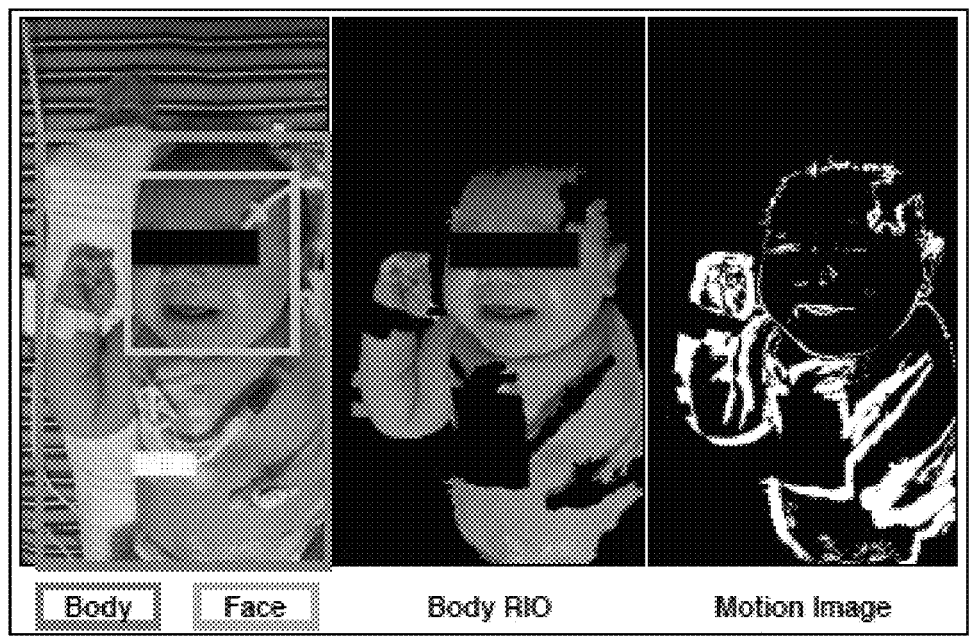
FIG. 17 illustrates photographic examples of region of interest (ROI) from sample input images.

In this embodiment, a temporal multimodal approach was investigated for assessing postoperative pain. The approach combined facial expression, body movement, and crying sound. The data of procedural and postoperative pain from the previous description was used for separately training different models corresponding to different pain indicators. For each pain indicator, spatiotemporal features were extracted and used to generate the score of that specific indicator. Then, the scores of all indicators were fused to generate the final pain level. FIG. 16 represents an overview of the proposed temporal multimodal approach for assessing postoperative pain.

In an exemplary embodiment of the multimodal spatiotemporal method of the present invention, the first pre-processing step involves extracting key-frames from all videos using FFmpeg library. The face region is then detected in each frame using a pre-trained YOLO-based face detector. The YOLO face detector was pre-trained using the WIDER face dataset, which contains around 393,703 faces. The total number of key-frames extracted from each video segment were fixed to 32 frames. Using a fixed number of frames is important because the number of key-frames in each video varies. Further, the face region in some key-frames was occluded, which causes the face detector to fail. Therefore, a fixed number of key-frames were used to facilitate the training process. Some key-frames were randomly dropped if the number of frames was larger than 32 and resampling techniques were used to generate more frames if the number was lower than 32. To enlarge the dataset prior to the CNNs training, image augmentation was performed on the key-frames using random composition of 30°, random rotation, ±25% brightness change, and horizontal flipping.

Deep learning-based architectures (e.g., VGG-Net) have been successfully used for detecting a wide range of emotions including pain. In this exemplary embodiment, a pre-trainedVGG-16 CNN architecture was fine-tuned to extract visual features from images captured during postoperative pain. Table VII shows the details of the fine-tuned VGG-16 architecture. Since empirical evidence showed that Bilinear CNN, as previously described, can better capture subtle changes, a Bilinear CNN was used with two VGG-16 streams to learn pain-related features. As shown in FIG. 16, the features extracted by both streams are then combined to generate the bilinear vector followed by two Fully Connected (FC) layers (64 units) and a dense layer (1 unit, linear activation). Also, Dropout layers (0.5) are added after each FC layers to prevent over-fitting. Two VGG-16 networks, which were pre-trained using VGGFace2 [4] and ImageNet [6] datasets, were used as the streams of the Bilinear CNN. The entire Bilinear CNN model was then fine-tunes using our procedural and postoperative dataset.

TABLE VII

Details of fine-tuned VGG-16 architecture.

| Layer Type | Configuration |
| --- | --- |
| Base mode | Before FC layer without Pooling |
| FC | Dense 512, Relu |
| Dropout | Dropout (0.5) |
| FC | Dense 512, Relu |
| Dropout | Dropout (0.5) |
| FC | Dense 1, Activation = Linear |

Pain is a dynamic event that evolves in a particular pattern over time. Hence, it is necessary to integrate temporal information to obtain an accurate assessment of pain. After extracting the features using the Bilinear CNN, the deep features are further trained by RNN to learn the pain dynamics. Specifically, LSTM network with the configuration shown in Table VIII was used. Two LSTM layers were used followed by two FC layers. Finally, a Dense layer with sigmoid activation was used to classify the signal as pain or no-pain. To prevent over-fitting, dropout layers were used, as shown in Table VIII.

TABLE VIII

Details of LSTM architecture.

| Layer Type | Configuration |
| --- | --- |
| RNN | LSTM 16, Activation = Tanh, Recurrent Activation = Hard Sigmoid, Dropout (0.2) |
| RNN | LSTM 16, Activation = Tanh, Recurrent Activation = Hard Sigmoid, Dropout (0.2) |
| FC | Dense 16, Relu |
| Dropout | Dropout (0.3) |
| FC | Dense 16, Relu |
| Dropout | Dropout (0.3) |
| FC | Dense 1, Activation = Sigmoid |

Similar to the previously described facial expression, the key-frames from the video segments were extracted using FFmpeg library. A YOLO detector was used, which was pre-trained originally on COCO dataset containing around 330K images from 80 object categories, to detect the body regions of neonates. Further, similar to facial expression, the number of key-frames was fixed to 32 from each video segment. The resampling technique helps to generate an equal number of frames in case of any failure detection. To enlarge the dataset for the CNN training, random composition was performed of 30°, random rotation, ±25% brightness change, and horizontal flipping.

The state-of-the-art methods for extracting pain-relevant features from body regions are handcrafted-based (e.g., motion image) and deep-learning-based (e.g., VGG-16). Therefore, two types of method were used, namely the motion image and VGG-16, to assess neonatal postoperative pain from body movement.

The motion image identifies the changes in pixels between consecutive frames, and it is calculated by subtracting consecutive frames followed by thresholding. Pixels of the motion image have a value of 1 (movement) and 0 (no movement). To calculate the total motion in each frame, all the pixels are summed together and divided by the frame's dimensions. The calculated total motion is then used as the main feature to train traditional classifiers such as Gaussian Naive Bayes, Random Forest, and K-Nearest Neighbors. For deep learning, trained the VGG-16 networks were trained using both the motion image and original body image. The configurations of the fine-tuned VGG-16 network are presented in Table VII. FIG. 7 shows different ROIs (Region of Interest) of a sample subject.

To capture the temporal changes of body movement, we integrated RNN (i.e. LSTM) network was integrated to VGG-16. The same LSTM network architecture (Table VII) was used, which was also used for the facial expression (see Table VII). The integration of VGG-16 and LSTM allows the system to learn body movement dynamics over time.

During the failure of recording a specific pain indicator due to occlusion or swaddle, crying sound can be used to assess pain. The state-of-the-art methods for extracting pain-relevant features from crying sounds are handcrafted-based (e.g., MFCC) and deep-learning-based (e.g., spectrogram image). Therefore, two types of features were extracted, MFCC, and deep features, and they were then used to assess neonatal postoperative pain.

MFCC, which stands for Mel Frequency Cepstral Coefficient (MFCC), is a popular Cepstral Domain method that has been successfully used to extract a useful and representative set of features (i.e., coefficients) from an audio signal while discarding noise and non-useful features. Taking the Inverse Fourier Transform (IFT) of the logarithm of the signal's spectrum converts the audio signal to the Cepstral Domain. 20 MFCCs features were extracted over all of the frames of an audio segment (approx. 9 seconds). The mean features from the 20 MFCCs were then calculated, which lead to a mean MFCCs feature vector length of 388.

In addition to MFCCs features, the raw audio signal (approx. 9 seconds) was converted to a spectrogram image. The spectrogram image shows the visual representation of a given audio signal. It represents the change of frequency components with respect to time and suppresses noise. Brighter pixels in the spectrogram image represent higher energy and vice versa. After generating the spectrogram image for each audio segment, deep features were extracted from these images using a VGG-16 network.

Figure 18:
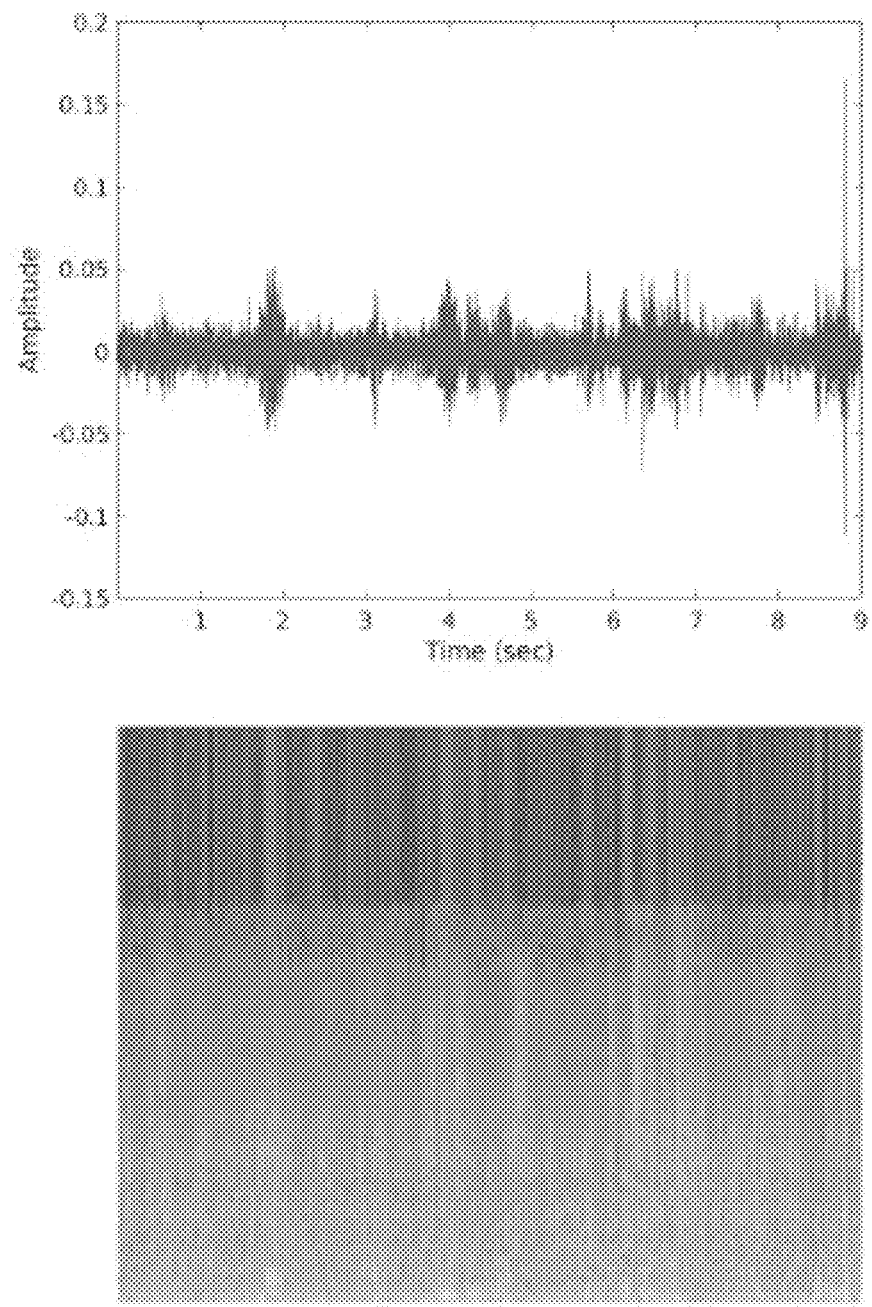
FIG. 18 illustrates an audio signal (top) and its corresponding spectrogram image (bottom) for a neonate during no-pain state.
Figure 19:
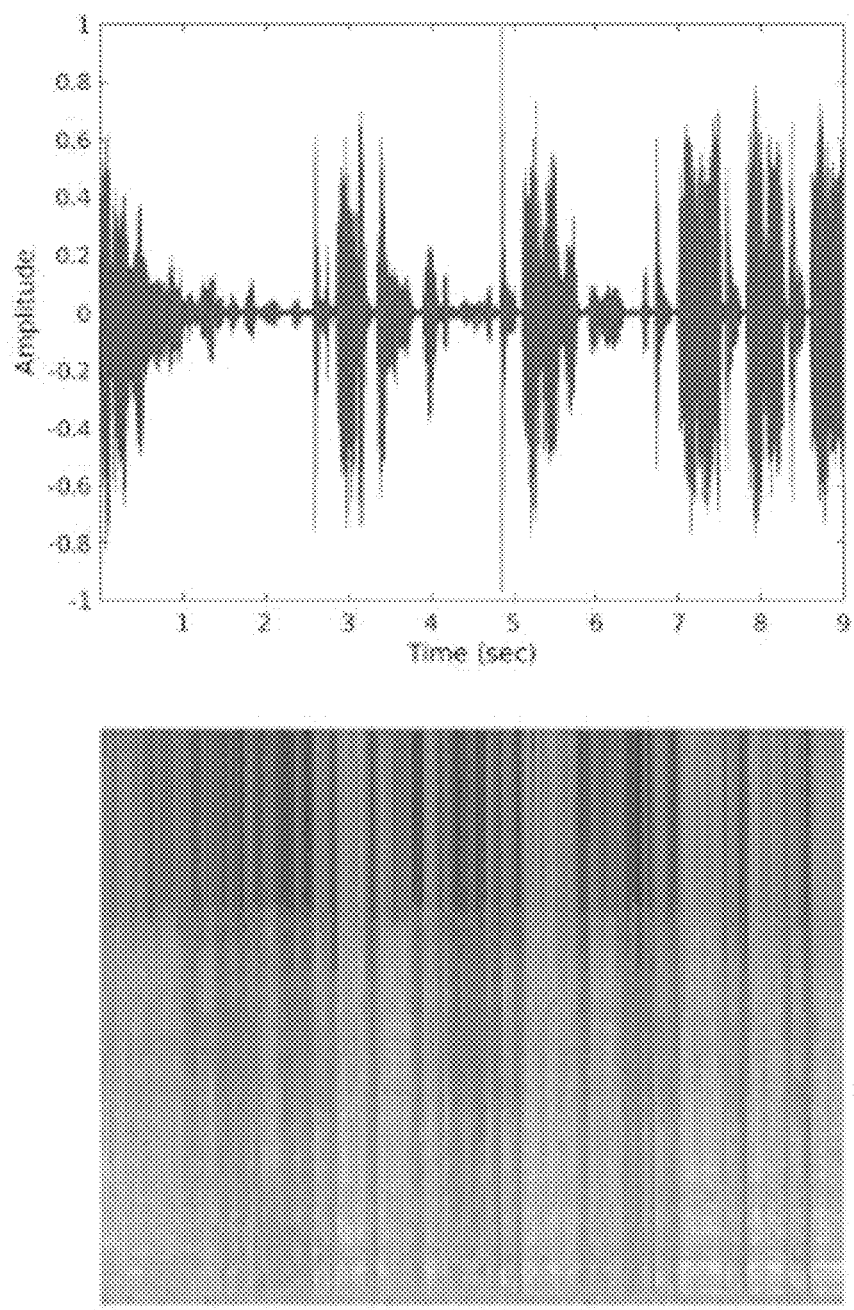
FIG. 19 illustrates an audio signal (top) and its corresponding spectrogram image (bottom) for a neonate during postoperative pain.

To train the network, the set of spectrogram images was enlarged by applying signal augmentation techniques to the original audio signal. Each audio signal was augmented by changing the raw frequency f at 3 different levels (f/3, f/2, 2f/3), and adding 6 different levels of noise (0:001, 0:003, 0:005, 0:01, 0:03, 0:05). Further, a combination of both frequency and noise was also applied to create more variant signals. This process generated a total of 27 (3+6+3*6) augmented images for each audio signal. FIG. 18 and FIG. 19 show examples of the raw audio signals and their corresponding spectrogram images during no-pain and pain states of a same subject.

Following the state-of-the-art methods, both traditional machine learning classifier and deep learning-based classifiers were used. In the case of the traditional classifier, such as Gaussian Naive Bayes, Random Forest and K-Nearest Neighbors (KNN) classifiers were trained using the extracted MFCCs features. For the deep learning-based classification, a pretrained (ImageNet) VGG-16 CNN network was used and the network was fine-tuned (similar to Table VII) using the postoperative pain dataset. The VGG-16 CNN network was trained using the spectrogram images extracted as described above. The last classification layer of the VGG-16 CNN has a sigmoid activation function instead of the linear activation.

To generate a multimodal assessment of postoperative pain, the pain scores generated by all indicator-specific models were combined together using decision fusion, as shown in FIG. 16. The multimodal pain assessment is necessary because pain manifests itself in different signals. In addition, the multimodal approach is necessary because it allows for the detection pain during the failure of recording some pain indicators, as discussed in the next section and shown in Table IV. To combine the labels or scores of facial expressions, crying sound, and body movement, an unweighted majority voting scheme was used in which was chosen the majority label in a given combination of labels as the final label. If the combination results in a tie, the class probability (confidence score) was used to break the tie.

In the following discussion, the performance of assessing neonatal postoperative pain using a single pain indicator at a time (unimodal) and multiple pain indicators together (multimodal) is presented. Before presenting the results, the process of extracting and preparing the videos is described followed by the training and evaluation protocols.

The aforementioned neonatal pain dataset was used to evaluate the proposed temporal multimodal approach. The dataset consists of both procedural (202 videos) and postoperative (218 videos) pain. A procedural dataset (balanced set of 116 samples) was used for pre-training the model (in case of face only) and the postoperative dataset was used for fine-tuning and evaluation. After performing the preprocessing steps, the total number of video segments (each has 9 seconds length) for each pain indicator in the postoperative dataset, were 187, 218, and 216 for face, body, and sound, respectively. Note that the face was missing in 31 videos (187/218) and the sound was missing in 2 videos (216/218).

Two types of training techniques were used: traditional classifiers training and deep learning. For both cases, the leave-one-subject-out protocol for was used for training and testing as this protocol is more realistic in case of clinical applications because it allows the capture of differences between patients. In the case of the traditional classifiers, a KNN classifier (K=3, determined empirically) and Random Forest classifier (N=100 determined empirically) was used. For deep learning, images (face image, body image, motion image, and spectrogram) of size 224×224 was used as input to individual VGG-16 models to extract deep features from each individual indicator as shown in FIG. 16. The extracted features are then fed to RNN networks to learn pain patterns and dynamics. Adam optimizer with a learning rate of 0.0001 was used to train the CNN and RNN models. A batch size of 16 and 1 were used for CNN and RNN respectively for up to 100 epochs. All the training was performed to minimize the validation loss following an early stopping strategy.

Two levels of training, in the case of deep learning, were performed. In the first level, the pain scores of each indicator (i.e., score 0 or 1 (face and body) and score 0, 1, or 2 (sound)) were used for training the CNN models. In the second level, the final pain labels, which are no-pain, moderate pain, and severe pain were used to train the RNN models. As previously discussed, these final pain labels are generated by summing the individual scores and thresholding. Note that the labels of moderate and severe pain were combined into a single pain class while training the RNN models because the number of instances with a moderate pain label is relatively smaller (33 examples).

To evaluate the performance of the trained models, the weighted accuracy, weighted precision, weighted recall, and F-1 score were used. Weighted metrics reflect the performance of each class as they report the fraction of the correct prediction for each class over the total number of samples; i.e., weighted metrics consider the instances of a specific class. In addition to these, the True Positive Rate (TPR), False Positive Rate (FPR) and Area Under the Curve (AUC) were calculated for the pain class.

The performance of using a single pain indicator, at one time, for postoperative pain assessment was evaluated. Both traditional machine learning-based approaches and deep learning-based approaches were used. Table IX shows the performance of using both traditional and deep learning approaches with a single pain indicator for assessing postoperative pain. In all indicators and in most cases, the approaches of the present invention outperformed the state-of-the-art methods by a large margin. As can be seen from Table X, crying sound indicator achieved the highest accuracy (79.63%) and outperformed the accuracies of body (70.50%) and face (69.52%). Similarly, crying sound indicator achieved the highest AUC (0.87) and outperformed the AUCs of body (0.78) and face (0.82).

TABLE IX

Unimodal and Multimodal assessment of neonatal postoperative pain using different traditional and deep learning approaches.

| Modality | Approach | Accuracy | Precision | Recall | F1-Score | TPR | FPR | AUC |
|---|---|---|---|---|---|---|---|---|
| Face | VGG16 + LSTM | 0.6203 | 0.6195 | 0.6203 | 0.6197 | 0.6634 | 0.4302 | 0.7300 |
|  | Bilinear VGG16 + LSTM | 0.6952 | 0.7084 | 0.6952 | 0.6834 | 0.8614 | 0.5000 | 0.9196 |
| Body | Motion + Gaussian NB | 0.6330 | 0.6562 | 0.6330 | 0.6189 | 0.4404 | 0.1743 | 0.5001 |
|  | Motion + Random Forest | 0.5872 | 0.5874 | 0.5872 | 0.5868 | 0.5596 | 0.3853 | 0.3382 |
|  | Motion + KNN | 0.5688 | 0.5697 | 0.5688 | 0.5675 | 0.5138 | 0.3761 | 0.3899 |

TABLE IX-continued

Unimodal and Multimodal assessment of neonatal postoperative pain using different traditional and deep learning approaches.

| Modality | Approach | Accuracy | Precision | Recall | F1-Score | TPR | FPR | AUC |
|---|---|---|---|---|---|---|---|---|
| | Motion Image + VGG16 + LSTM | 0.6835 | 0.6906 | 0.6835 | 0.6805 | 0.7799 | 0.4128 | 0.7323 |
| | Body ROI Image + VGG16 + LSTM | 0.7050 | 0.7047 | 0.7050 | 0.7047 | 0.7333 | 0.3263 | 0.7786 |
| Sound | MFCC + Gaussian NB | 0.6296 | 0.6328 | 0.6296 | 0.6267 | 0.5421 | 0.2844 | 0.4194 |
| | MFCC + KNN | 0.6991 | 0.7001 | 0.6991 | 0.6988 | 0.7290 | 0.3303 | 0.3592 |
| | MFCC + Random Forest | 0.7269 | 0.7362 | 0.7269 | 0.7245 | 0.8224 | 0.3670 | 0.4459 |
| | Spectrogram Image + VGG16 | 0.7963 | 0.7964 | 0.7966 | 0.7963 | 0.7850 | 0.1927 | 0.8690 |
| Multimiodal | (F + B + S) + Decision Fusion | 0.7936 | 0.8028 | 0.7936 | 0.7920 | 0.8807 | 0.2936 | 0.9010 |

Precision, Recall, and F-1 score are weighted by both classes.
TPR, FPR, and AUC are calculated for the pain class.
Bold texts indicate our approaches and bold values indicate superiority.
Bold text (F + B + S) represents the best from the unimodal (bold texts) approaches.

To understand these results, the data was observed, and it was found that sound has less noise as compared to face and body in the dataset of postoperative neonates. Specifically, neonates' faces in the NICU are usually occluded (partial or complete) by oxygen's masks, tapes, or due to a prone sleeping position. In case of body, some neonates are swaddled while others show weak movements due to sedation or exhaustion. In summary, one can conclude from the Table X that crying sound can better assess postoperative pain as compared to facial expression and body movement. In addition, one can conclude that the proposed approaches of the present invention for analyzing facial expression, sound, and body show better performance, in terms of accuracy, precision, recall, TPR, FPR, and AUC, as compared to the traditional approaches.

generated using the best approach for each indicator (best approaches are bolded in the second column of Table X) were combined. Table IX shows the results of fusing (decision-level) the labels of face, body, and sound. Recall that the numbers of video instances for face, body, and sound are 187, 218, and 216, respectively. This means that some indicators would be missing when one combines all of them together to generate the multimodal assessment. As shown in Table IX, the multimodal approach achieved better overall performance as compared to the unimodal approach. The reason for the high performance of sound can be attributed to the fact that this indicator has less noise and a larger number of instances as compared to other indicators (e.g., facial expression). Although crying sound has a performance comparable to the multimodal approach, it is believed that

TABLE X

Unimodal and Multimodal neonatal assessment of postoperative pain (all pain indicators are present).

| Metric | Face | Body | Sound | Face + Body | Body + Sound | Sound + Face | Face + Body + Sound |
|---|---|---|---|---|---|---|---|
| Accuracy | 0.7076 | 0.6667 | 0.7661 | 0.7076 | 0.7719 | 0.6901 | 0.7895 |
| Precision | 0.7119 | 0.6645 | 0.7682 | 0.8071 | 0.8274 | 0.7032 | 0.7913 |
| Recall | 0.7076 | 0.6667 | 0.7661 | 0.7076 | 0.7719 | 0.6901 | 0.7895 |
| F-1 Score | 0.6970 | 0.6650 | 0.7667 | 0.6630 | 0.7522 | 0.6703 | 0.7863 |
| TPR | 0.8557 | 0.7320 | 0.7732 | 1.0000 | 0.9897 | 0.8866 | 0.8761 |
| FPR | 0.4865 | 0.4189 | 0.2432 | 0.6757 | 0.5135 | 0.5676 | 0.3243 |
| AUC | 0.8082 | 0.7778 | 0.8239 | 0.8353 | 0.8763 | 0.8396 | 0.8791 |

Precision, Recall, and F-1 score are weighted by both classes.
TPR, FPR, and AUC are calculated for the pain class.
Bold values indicate superiority.

In addition, it can also be observed that temporal information integration greatly improves the performance of the pain assessment. Existing work did consider the feature, only frame-by-frame. However, in the present invention, temporal information (over frames) was integrated, which led to better performance in the case of all approaches. In the case of body, inclusion of the LSTM network shows AUC of 0.78 and 0.73 which was a jump from 0.50. Also, in the case of sound, the spectrogram image shows better performance compared to the MFCC features due to better temporal information integration.

The unimodal approach uses one single indicator at a time to predict the pain class. In practice, there are cases where face and body are not visible. For example, the baby's face can be wrapped with tape and the body can be swaddled. In such cases, the multimodal assessment of the present invention provides a reliable solution. To investigate the impact of the multimodal approach on postoperative pain assessment, the scores or labels of different pain indicators, which are the multimodal approach is necessary because pain manifests itself in different signals.

Figure 20:
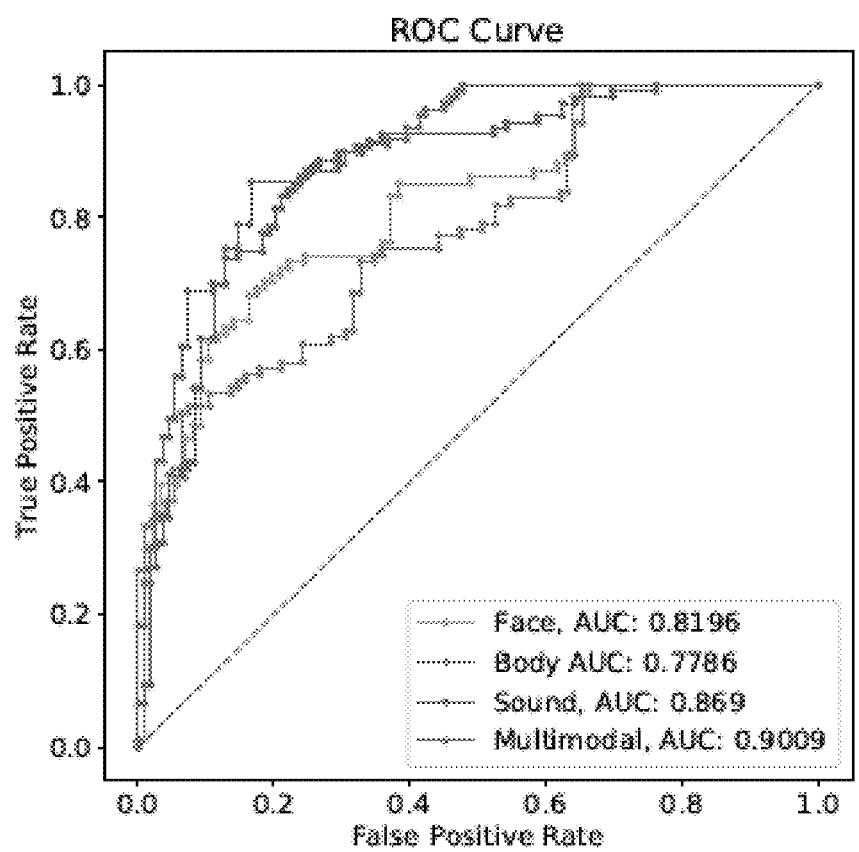
FIG. 20 illustrates ROC curves of different approaches, in accordance with embodiments of the present invention.

In addition, the multimodal approach allows for the assessment of pain during circumstances when sounds signals are missing due to noise, sedation, or individual differences (e.g., some neonates do not cry but move their arms/legs during pain). FIG. 20 provides visualization of the ROC curve of Table IX. It can be observed that the multimodal approach achieves a better performance (curve) as compared to individual modalities.

To make a more reliable and fair comparison, the experiments were further extended by making sure that there are no missing indicators; i.e., 171 samples from the dataset were selected, where all the pain indicators are present. Table X presents the performance of the multimodal when all indicators are present. Table X also presents the performance of unimodal (single indicator at a time) and different combinations of pain indicators using 171 samples. It can be observed that in most cases the multimodal achieved the best performance. In the final experiment, 25% of samples were randomly dropped from each indicator to assess the robustness of the multimodal approach of the present invention. Random dropping by 25% was performed ten times and reported the average performance in Table XI. From the Table XI, one can conclude that the multimodal results are consistent over all indicators and perform better than the unimodal method. These results are consistent with previous clinical findings and suggest that the automated multimodal approach for assessing postoperative pain is more efficient, in terms of performance and robustness, as compared to the unimodal approach.

TABLE XI

Unimodal and Multimodal assessment of neonatal postoperative pain (randomly dropping 25% samples from each indicator 10 times).

| | Face | | Body | | Sound | |
| --- | --- | --- | --- | --- | --- | --- |
| Metric | Unimodal | Multimodal | Unimodal | Multimodal | Unimodal | Multimodal |
| Accuracy | 0.7124 ± 0.03 | 0.7913 ± 0.01 | 0.6610 ± 0.02 | 0.7649 ± 0.01 | 0.7742 ± 0.01 | 0.7784 ± 0.01 |
| Precision | 0.7218 ± 0.03 | 0.7988 ± 0.01 | 0.6596 ± 0.02 | 0.7692 ± 0.01 | 0.7764 ± 0.01 | 0.7908 ± 0.01 |
| Recall | 0.7124 ± 0.03 | 0.7913 ± 0.01 | 0.6610 ± 0.02 | 0.7650 ± 0.01 | 0.7742 ± 0.01 | 0.7784 ± 0.01 |
| F-1 Score | 0.7035 ± 0.03 | 0.7859 ± 0.01 | 0.6591 ± 0.02 | 0.7593 ± 0.01 | 0.7746 ± 0.01 | 0.7705 ± 0.01 |
| TPR | 0.8563 ± 0.03 | 0.9052 ± 0.02 | 0.7282 ± 0.03 | 0.8784 ± 0.00 | 0.7819 ± 0.03 | 0.9155 ± 0.02 |
| FPR | 0.4612 ± 0.04 | 0.3581 ± 0.03 | 0.4250 ± 0.03 | 0.3838 ± 0.02 | 0.2358 ± 0.03 | 0.4014 ± 0.03 |
| AUC | 0.8093 ± 0.02 | 0.8724 ± 0.01 | 0.7739 ± 0.02 | 0.8675 ± 0.01 | 0.8288 ± 0.02 | 0.8682 ± 0.01 |

Precision, Recall, and F-1 score are weighted by both classes.
TPR, FPR, and AUC are calculated for the pain class.
Bold values indicate superiority.

In various embodiments, as described above, the present invention provides a temporal multimodal AI-based system and method for assessing postoperative pain in neonates. The proposed system uses video (face, body) and audio (crying sound) signals individually to generate pain scores. These scores are then combined using a decision fusion to predict the final pain assessment. The experimental results suggest that the multimodal approach of the present invention is more reliable for assessing postoperative pain in a real-world clinical environment. It is believed that the proposed approach can significantly enhance the current practice for assessment, which is discontinuous, inconsistent, highly depends on the nurses' experience and subjectivity, and is often limited by the lack of medical resources.

Figure 21:
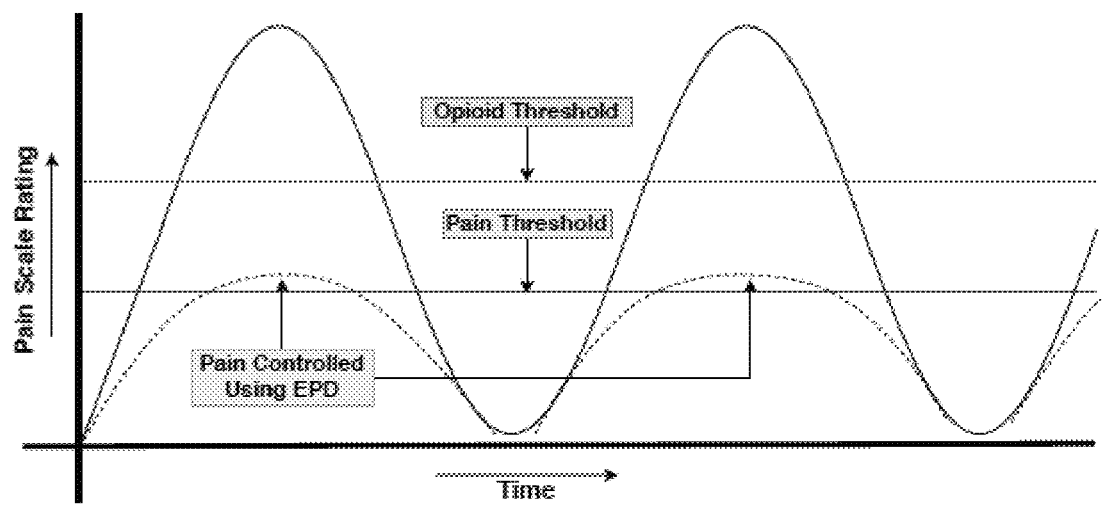
FIG. 21 is an illustration of the potential benefits of EPD in neonates.

In a particular embodiment utilizing the spatiotemporal multimodal AI-based system and method of the present invention, a machine learning-based system and method are provided for continuous and objective Early Pain Detection (EPD) in neonates. As shown in FIG. 21, the subjective assessment of facial expression of neonates may not be sufficient to detect pain prior to a critical threshold. In contrast, the Early Pain Detection (EPD) system and method of the present will be effective in predicting the pain that will be experienced by the neonate prior to the pain reaching the pain threshold.

In FIG. 32, the schematic illustrates how pain prediction prior to pain onset could create a time window (~30 to 40 minutes) for controlling pain using fast-acting, non-opioid pain medications., e.g. intravenous acetaminophen or ibuprofen. The goal of EPD is to "flatten the curve" for the recurring cycle of intermittent post-surgical pain, narcotic treatment and opioid withdrawal (as shown by larger peaks and valleys), leading to less toxic stress (smaller peaks and valleys) on babies in NICU.

In order to identify areas in need for technology development in the field of neonatal pain management, in-person interviews of over three dozen clinical staff affiliated with three NICUs at local hospitals in the Tampa Bay region (Tampa General Hospital, St. Joseph's Hospital, Johns Hopkins Children's Hospital) were performed. From these interviews it was learned that current pain management of newborns in NICUs can be generally characterized as manual, subjective, and discontinuous. Currently, NICU nurses treat neonates emerging from post-surgical sedation with pain management plans based on intermittent, subjective ratings with poor inter-rater agreement. Further, in the vast majority of cases newborns undergo pain mitigation with highly addicting Schedule II narcotics (morphine, fentanyl) that require 4-5 extra days for opioid withdrawal. All clinical staff interviewed favored the development and use of early pain detection (EPD) over the current approach for NICU-based management of prolonged post-surgical pain in neonates. The major reasons given for positive impacts of EPD on short- and long-term health outcomes in this vulnerable population are described below.

It is believed EPD based on an AI framework could relieve the current burden on NICU clinical staff who must rely on subjective qualitative and semiquantitative pain assessment scales as the basis for pain management in newborns.

FIG. 21 represents a typical example of pain scale rating of a NICU patient. The blue line indicates the pain threshold to consider the signal as a pain signal and red line indicates the opioid threshold to apply opioid to control the pain. EPD technology can help to predict the future pain earlier based on previous and current data. As a result, using the normal medication, caregivers will be able to control the pain earlier so that it does not reach too much to use the opioid. Thus, EPD technology could lead to avoiding opioid addiction.

In contrast to pain assessment, tools for predicting time to pain onset creates an opportunity to intervene with both nonopioid and non-pharmaceutical approaches prior to pain onset. Such interventions, if effective, have the potential to avert damage to the neonate's developing central and peripheral nervous systems caused by both pain and withdrawal from opioid-based medications for pain mitigation.

Figure 22:
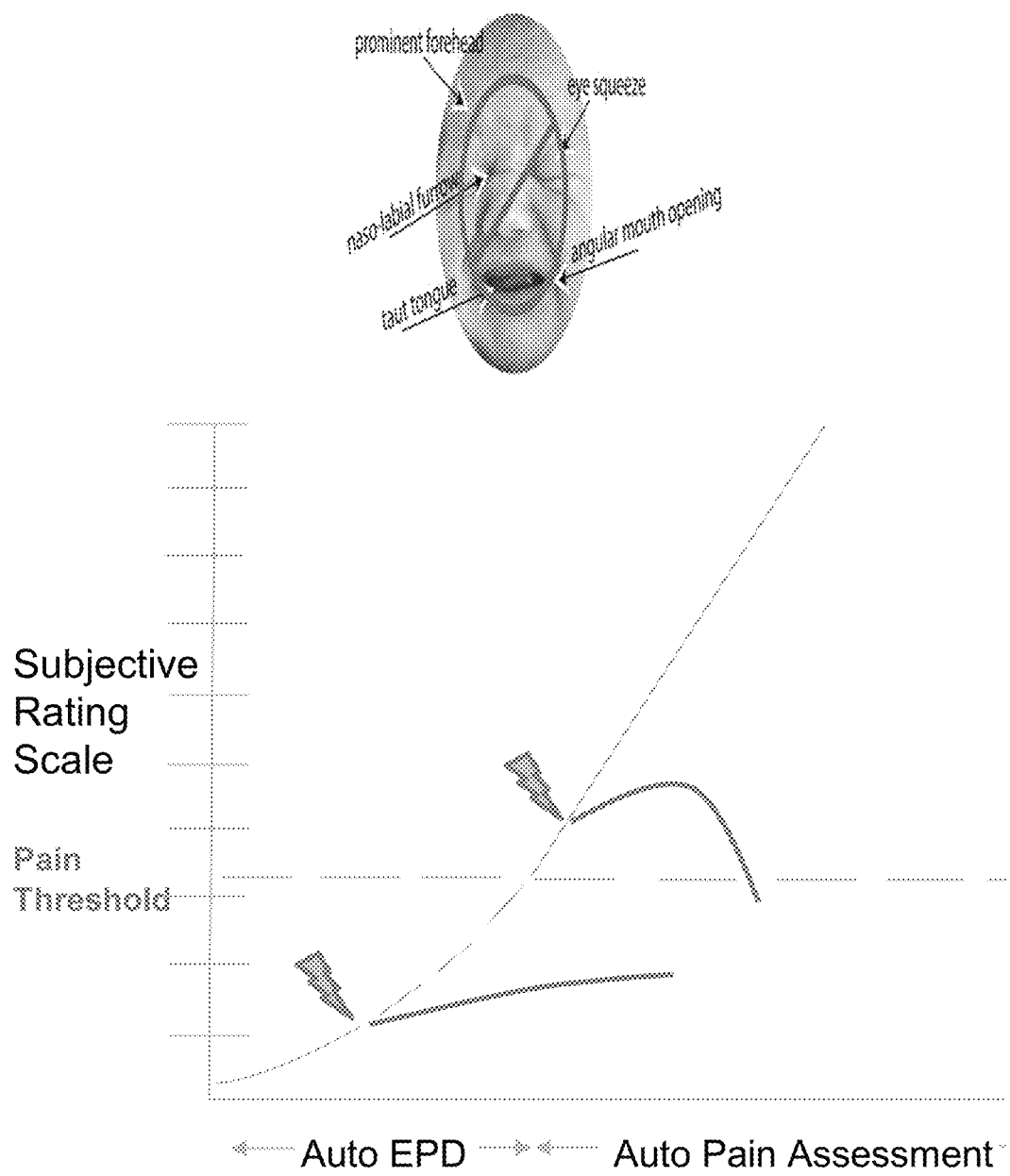
FIG. 22 is a graphical illustration of the goal of an EPD system to support continuous and objective monitoring of neonatal pain that will allow a minimum of ←30 minutes prior to pain onset for pain mitigation.

As illustrated in FIG. 22, the goal of an EPD system is to support continuous and objective monitoring of neonatal pain that will allow a minimum of ←30 minutes prior to pain onset for pain mitigation using non-addicting drugs, including, but not limited to, acetylminophen and nonsteroidal anti-inflammatory drugs (NSAIDS), rather than opioid medications, such as fentanyl and morphine. If EPD can reduce or avoid the need for severe pain and opioid medications in the majority of cases, the EPD could substantially reduce the consequences of long-lasting toxic stress trauma including behavioral impairments, epigenetic modifications and increased complications caused by extreme pain and opioid addiction on neonates in NICU. Finally, it is expected that EPD will achieve these treatment goals while decreasing the economic burden on patients, private hospitals and government agencies by reducing the length of stay for treatment of opioid withdrawal.

Machine learning techniques have already shown substantial progress in neonatal pain assessment, as previously described. Based on this evidence it can be estimated that AI can also predict the pain earlier in the future. Similar to weather analyses that gathers multimodal variables for making predictions, "there's a 90% chance of rain in ←5 minutes," machine learning-based methods can utilize the neonate's facial expressions, body movements, crying frequency and vital sign data (e.g., heart rate, blood pressure, oxygen saturation level) to assign a probability of experiencing pain, "there's a 90% chance this neonate will experience prolonged surgical pain in ←25 minutes." Deep features using CNNs can be extracted from different modality and temporal pain dynamics learned by Recurrent Neural Network (for example: LSTM) or Reinforcement Learning. Moreover, based on the patient history (i.e. previous medical condition, family history, medication, genetic) the AI model can boost up its learning performance and predict future pain estimation earlier more efficiently.

Figure 23:
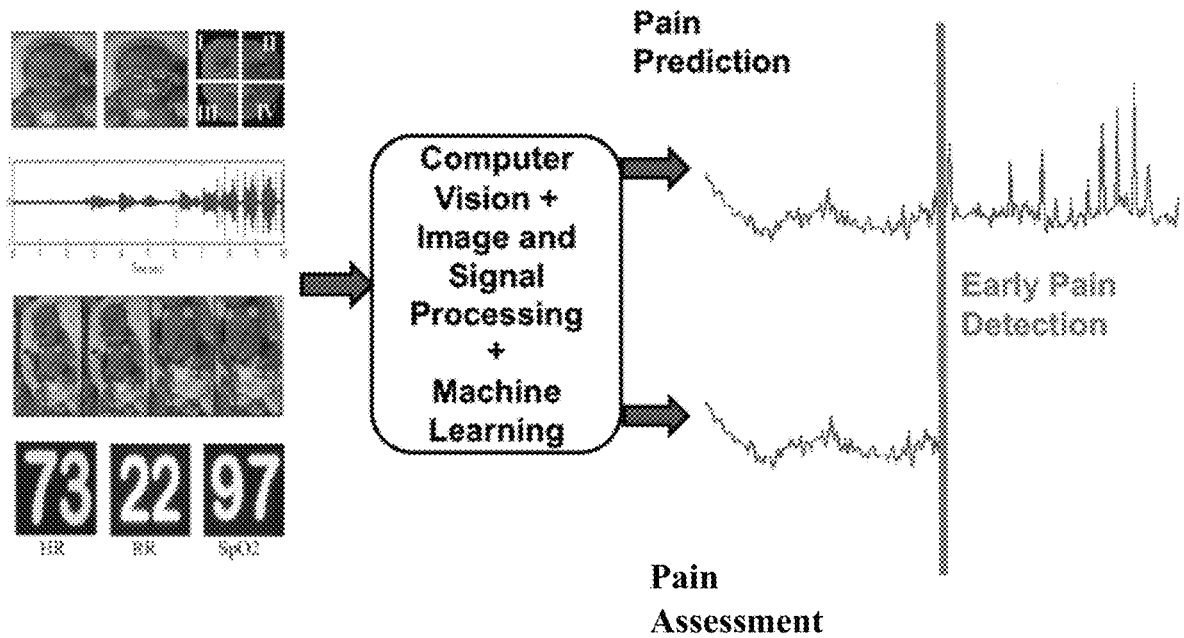
FIG. 23 is a diagrammatic illustration of an AI system for EPD in neonates, in accordance with an embodiment of the present invention.

A system for providing EPD in neonates requires minimal hardware components, which includes a data reading device (e.g., A/V recorder such as a camera and/or microphone, vital signs reader) for visualizing and recording the neonate's facial expressions, voice, vital signs and body movement including arms/legs (FIG. 23). A facial expression classifier is used for evaluating the pain via the facial expressions, where the facial expression classifier produces a facial expression score, a voice classifier for evaluating the pain via the infant's crying, where the voice classifier produces a voice score based on the frequency and pitch of those inarticulate sounds (e.g., using speech signal analysis). A vital signs classifier evaluates the neonate's pain according to its physical condition (e.g., heart rate, breathing rate, oxygen saturation, changes in cerebral deoxyhemoglobin concentration, etc.), using a vital signs classifier that produces a vital signs score. The system software includes a processor that runs a machine learning algorithm (e.g., parametric, non-parametric, optical flow, facial strain, local binary patterns, linear predictive coding, linear regression, neural network) for processing images, videos, signals, and/or a combination thereof. The facial expression score, voice classifier score, body motions score, and vital signs score are combined/weighed to produce a total score for pain assessment. The system also includes an output device, e.g., meter, LED indicator, for outputting the total score to NICU personnel for pain assessment.

FIG. 23 shows an approach of future EPD technology. Multimodal data from NICU patient such as facial expression, body movement, crying sound, and physiological signals can be used by AI algorithms (i.e. computer vision, signal processing, and machine learning altogether) to simultaneously assess pain and predict it before it occurs.

As such, AI-based frameworks using continuous monitoring of multiple modalities could provide the necessary tools for creating a time-window to pain onset. Such a time window could support safer, i.e., non-addicting pharmaceutical and non-pharmaceutical, interventions aimed at avoiding or minimizing damage to the neonate from both pain and opioid withdrawal.

With reference to FIG. 23, the machine learning-based technology of the present invention utilizes various multimodal inputs from the Neonatal Intensive Care Unit (NICU) or the Pediatric Intensive Care Unit (PICU). As in the previously described embodiments, the proposed EPD system observes facial expression, crying sound, body movement, and different vital sign signals.

In one particular embodiment, the N-PASS (Neonatal Pain, Agitation, and Sedation Scale) pain scale which considers crying/irritability, behavior/state, facial expression, extremities/tone, and vital signs (heart rate, blood pressure, respiratory rate, and oxygen saturation) of the babies is followed. The N-PASS pain scale also provides a score for sedation. The proposed EPD method provided by the present invention will use the machine learning-based solution to provide the continuous pain assessment of each modality and, based on the current assessments, it will predict the future pain signal continuously.

Figure 24:
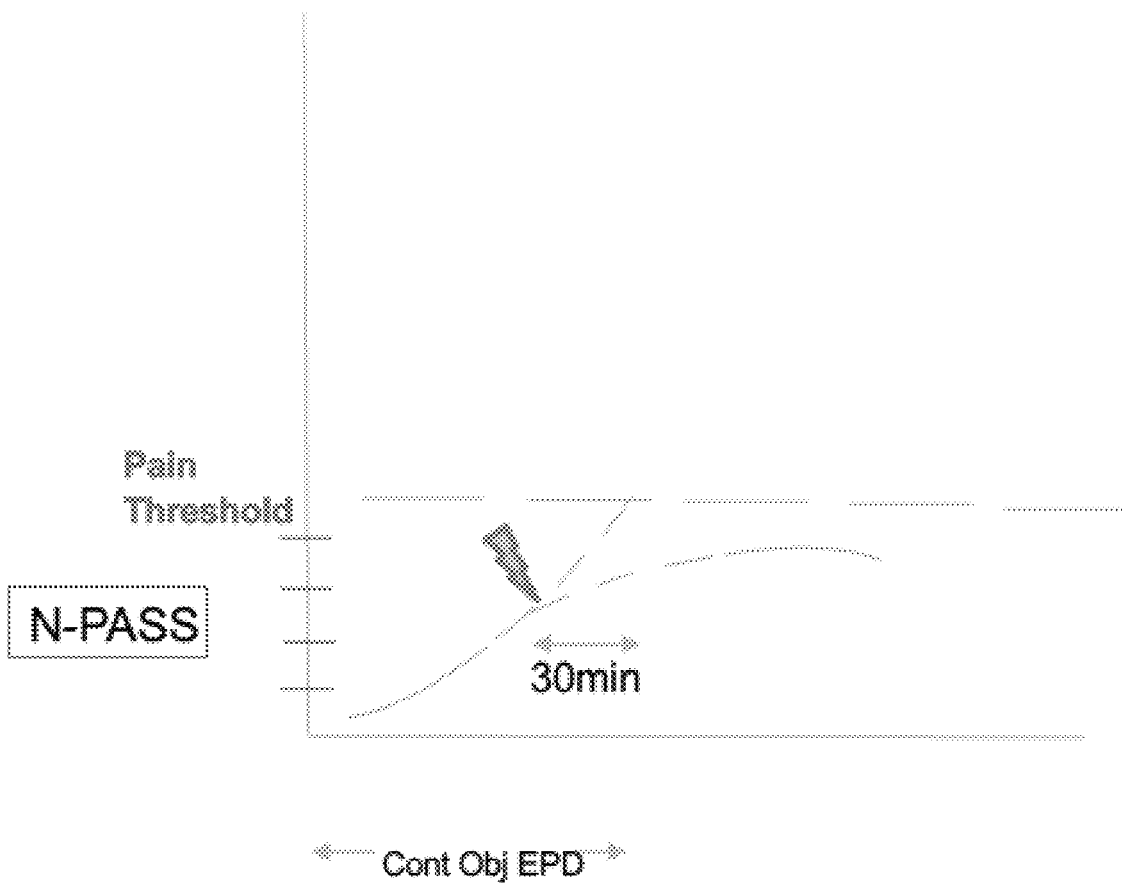
FIG. 24 is a graphical illustration of the collection of ground truth for EPD machine learning, in accordance with an embodiment of the present invention.

With reference to FIG. 24, in one embodiment, the system will use the N-PASS score provided by the NICU nurse to train the networks. It will generate the current pain assessment and will use the current pain objective assessment to predict future pain objective assessment (pain score).

In a specific hardware embodiment, GoPro camera or equivalent camera will continuously observe the neonates or infants and record the video and audio signals of the babies (facial expression and body movement). Different vital signs signals will also be collected via the camera followed by image processing techniques or directly from the medical electronic records. All of these signals will be passed to the EPD software and EPD will use its machine learning solution (which is trained before) to assess the current pain and predict the future pain signals. In the EPD software current and future pain monitoring signals will be shown continuously.

The various embodiments of the system and method of the present invention provide continuous individual pain objective assessment of each modality and based on the current assessment of each modality, the system will predict the future pain signal, in a continuous manner.

Hardware and Software Infrastructure Examples

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

Glossary of Claim Terms:

A/V recorder: This term is used herein to refer to a device that receives audio and/or video data. Examples include, but are not limited to, video cameras, sound recorders, etc.

Arousal state: This term is used herein to refer to the condition of the subject's physiological alertness, wakefulness, and attentiveness.

Behavior state: This term is used herein to refer to the condition or pattern of the subject's movements or conduct, and/or the subject's reactions or behaviors during a stimulus.

Body movement classifier: This term is used herein to refer to a module of the system that analyzes and classifies the physical motions of the subject's body into different patterns.

Body movement score: This term is used herein to refer to a value given to the subject's spatial motions upon an automated analysis of those motions, where the score is an indicator of pain felt by the subject.

Data reading device: This term is used herein to refer to any device that is capable of receiving data in the form of audio, video, body measurements, and other pieces of relevant data.

Digital mask: This term is used herein to refer to a digital capture of landmarks on the subject's face. For example, the mask can detect the subject's nose, thus "capturing" the nose, and then can be expanded to include the subject's eyes.

Expression recognition: This term is used herein to refer to an identification or observation of the subject's facial motions.

Expression segmentation: This term is used herein to refer to separation out the expression(s) on a subject's face by capturing the optical strain corresponding to elastic distortions of the facial skin tissue.

Extremities tone: This term is used herein to refer to the general condition of the subject's arms and legs. For example, the subject's arms/legs can be stretched out and tight, flexed, curled up, relaxed, etc.

Facial detection: This term is used herein to refer to computer technology that is capable of recognizing or identifying the subject's face from digital images or video.

Facial expression classifier: This term is used herein to refer to a module of the system that analyzes the facial movements/motions of the subject.

Facial expression score: This term is used herein to refer to a value given to the subject's facial movements/motions upon an automated analysis of those movements/motions, where the score is an indicator of pain felt by the subject.

Facial expressions: This term is used herein to refer to any movement or motion of the muscles beneath the skin of the face of the subject.

Facial strain: This term is used herein to refer to the tightness of the muscles of the subject's face.

Frequency-based features: This term is used herein to refer to the characteristics of sounds that relate to the frequency of those sounds, so that the characteristics can be extracted and analyzed.

Inarticulate sounds: This term is used herein to refer to noises made by the subject, where the noises are not expressed in normal words/language, such that there is no immediate clarity of the message based on the noises made.

Landmarks: This term is used herein to refer to recognizable features on the subject's face. An example is the subject's nose, perhaps because it protrudes out of the face.

Machine learning algorithm: This term is used herein to refer to the function behind recognizing particular patterns and applying artificial intelligence to make predictions from a given set of data.

Motions corresponding to pain: This term is used herein to refer to spatial movement of the subject's body, in particular the subject's extremities, Output device: This term is used herein to refer to any apparatus that can transmit a particular finding, conclusion, or data to a user or operator thereof.

Overall strain magnitude: This term is used herein to refer to the level or extent of tightness of the muscles of the subject's face.

Pain intensity: This term is used herein to refer to the strength of an unpleasant sensation experienced by an individual or subject.

Peak detector: This term is used herein to refer to a function that segments the subject's facial expressions by finding the points of maximum strain.

Physical condition: This term is used herein to refer to the state of the subject body's basic functions. Examples include, but are not limited to, heart rate, respiratory rate, oxygen saturation, temperature, etc.

Subject that is incapable of clearly orally communicating said pain intensity or that is capable of communicating said pain intensity through only a behavioral indicator:

This term is used herein to refer to an individual who cannot physically speak or otherwise communicate pain in a manner that is absolutely clear to another individual. For example, an infant cannot speak or otherwise clearly communicate pain, other than by using behavior, such as body motions, vital signs, crying, etc.

Vital signs classifier: This term is used herein to refer to a module of the system that analyzes the physical condition of the subject.

Vital signs reader: This term is used herein to refer to any device that is capable of receiving data about vital signs of a subject or individual.

Vital signs score: This term is used herein to refer to a value given to the subject's physical condition upon an automated analysis of that physical condition, where the score is an indicator of pain felt by the subject.

Voice classifier: This term is used herein to refer to a module of the system that analyzes the inarticulate sounds of the subject.

Voice score: This term is used herein to refer to a value given to the subject's inarticulate sounds upon an automated analysis of those sounds, where the score is an indicator of pain felt by the subject.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A system for predicting future pain that may be experienced by a subject, the systema comprising:
    an audio/video (A/V) recorder for recording video of facial expressions and body movements of the subject and for recording audio of sounds made by the subject;
    a vital signs reader to record vital signs of the subject;
    a facial expression classifier for evaluating the facial expressions of the subject recorded by the A/V recorder, the facial expression classifier producing a facial expression pain score based on the facial expressions of the subject;
    a body movement classifier for evaluating the body movements of the subject recorded by the A/V recorder, the body movement classifier producing a body movement pain score based on the body movements of the subject;
    a voice classifier for evaluating the sounds made by the subject recorded by the A/V recorder, the voice classifier producing a voice pain score based on the sounds made by the subject;
    a vital signs classifier for evaluating the vital signs of the subject recorded by the vital signs reader, the vital signs classifier producing a vital signs pain score based on the vital signs of the subject;
    a processor running a machine learning algorithm processing the facial expression pain score, the body movement pain score, the voice pain score and the vital signs pain score of the subject, and for combining the facial expression pain score, the body movement pain score, the voice pain score, and the vital signs pain score to produce a future pain probability signal, wherein the future pain probability signal includes a percentage probability and an associated time duration within which the subject will experience pain; and
    an output device for outputting the future pain probability signal.

2. The system as in claim 1, wherein the future pain probability score exceeds a predetermined threshold.

3. The system as in claim 2, wherein a therapy or intervention is indicated by the future pain probability signal exceeding the predetermined pain threshold.

4. The system as in claim 1, wherein the processor running the machine learning algorithm is trained based upon an N-PASS (Neonatal Pain, Agitation, and Sedation Scale) pain scale.

5. The system as in claim 1, wherein the A/V recorder comprises a video camera, and a microphone.

6. The system as in claim 1, wherein the motions of the subject indicate one or more of a behavior state, an arousal state and an extremities tone.

7. The system as in claim 1, wherein the vital signs includes a heart rate of said subject.

8. The system as in claim 1, wherein the subject is an infant.

9. The system as in claim 1, wherein the facial expression classifier evaluates the facial expressions of the subject based on facial strain of the subject by:
    generating the facial strain for a plurality of facial expressions of the subject; and
    training k Nearest-Neighbor (KNN) and support vector machine (SVM) to classify facial expressions of the subject as pain or no-pain.

10. The system as in claim 9, wherein performing expression recognition includes:
    generating an optical flow vector for each region of the subject's face, wherein the optical flow vector is used to estimate optical strain for each region;
    summing the estimated optical strains for each region to generate an overall strain magnitude, wherein the overall strain magnitude is related to the facial expressions that can indicate future pain that may be experienced by the subject.

11. The system as in claim 9, wherein performing expression recognition includes:
    applying a peak detector to detect points of maximum strain, wherein the maximum strain is related to the facial expressions that can indicate future pain that may be experienced by the subject.

12. The system as in claim 1, further comprising:
the facial expression classifier segmenting the subject's face into regions in order to provide the facial expression score, and where one or more regions are obstructed or occluded; and
the facial expression classifier performing facial detection where the face of the subject is detected, performing expression segmentation where the detected subject's face is segmented into regions, and performing expression recognition of the segmented regions to detect pain of the subject.

13. The system as in claim 12, wherein performing the facial detection further comprises, detecting landmarks on the subject's face to detect the subject's face, wherein the landmarks includes a nose on the subject's face, and wherein a digital mask is expanded around the nose to include eyes and a surrounding area of the subject's face.

14. The system as in claim 13, further comprising:
training the facial expression classifier using positive images including the landmarks and negative images not including the landmarks.

15. The system as in claim 1, wherein the subject is an infant, and wherein the sounds are crying by the infant.

16. The system as in claim 15, wherein speech signal analysis is used to recognize emotions expressed in the crying by the infant.

17. The system as in claim 1, wherein frequency-based features are extracted from the sounds to represent audio segments that are used to train the voice classifier.

18. The system as in claim 1, further comprising:
the vital signs of the subject further include breathing rate and oxygen saturation in blood of the subject.

19. A method for predicting future pain that may be experienced by a subject, the system comprising:
recording, with an audio/video (A/V) recorder, facial expressions, sounds, and body, movements of the subject, wherein said A/V recorder comprises a video camera for recording video of the facial expressions and body movements and a microphone for recording sounds of the subject;

recording, with a vital signs reader, vital signs of said subject;

evaluating, with a facial expression classifier, the facial expressions of the subject recorded by the audio/video recorder, the facial expression classifier producing a facial expression pain score based on the facial expressions of the subject;

evaluating, with a voice classifier, the sounds made by the subject recorded by the audio/video recorder, the voice classifier producing a voice pain score based on the sounds made by the subject;

evaluating, with a vital signs classifier, the vital signs of the subject, the vital signals classifier producing a vital signs pain score based on the vital signs recorded by the vital signs reader;

evaluating, with a body movement classifier, the body movements of the subject recorded by the A/V recorder, the body movement classifier producing a body movement pain score based on the body movements of the subject;

processing, by a processor running a machine learning algorithm, the facial expression pain score, the voice pain score and the vital signs pain score of the subject and combining the facial expression pain score, the voice pain score, the vital signs pain score and the body movement pain score to produce a future pain probability signal, wherein the future pain probability signal includes a percentage probability and an associated time duration within which the subject will experience pain.

20. The method as in claim 19, wherein the future pain probability score exceeds a predetermined threshold.

* * * * *